US010501739B2

(12) United States Patent
Eastburn

(10) Patent No.: US 10,501,739 B2
(45) Date of Patent: Dec. 10, 2019

(54) METHOD, SYSTEMS AND APPARATUS FOR SINGLE CELL ANALYSIS

(71) Applicant: Mission Bio, Inc., South San Francisco, CA (US)

(72) Inventor: Dennis Jay Eastburn, Burlingame, CA (US)

(73) Assignee: Mission Bio, Inc., South San Francisco, CA (US)

( * ) Notice: Subject to any disclaimer, the term of this patent is extended or adjusted under 35 U.S.C. 154(b) by 0 days.

(21) Appl. No.: 16/169,959

(22) Filed: Oct. 24, 2018

(65) Prior Publication Data

US 2019/0112595 A1 Apr. 18, 2019

Related U.S. Application Data

(63) Continuation-in-part of application No. 16/164,595, filed on Oct. 18, 2018.

(60) Provisional application No. 62/576,455, filed on Oct. 24, 2017, provisional application No. 62/574,109, filed on Oct. 18, 2017, provisional application No. 62/574,103, filed on Oct. 18, 2017, provisional application No. 62/574,104, filed on Oct. 18, 2017.

(51) Int. Cl.
C12N 15/10 (2006.01)
C12Q 1/6874 (2018.01)

(52) U.S. Cl.
CPC ....... *C12N 15/1065* (2013.01); *C12Q 1/6874* (2013.01)

(58) Field of Classification Search
None
See application file for complete search history.

(56) References Cited

U.S. PATENT DOCUMENTS

| | | | |
|---|---|---|---|
| 7,638,276 B2 | 12/2009 | Griffiths et al. | |
| RE41,780 E | 9/2010 | Anderson et al. | |
| 8,067,159 B2 | 11/2011 | Brown et al. | |
| 8,257,925 B2 | 9/2012 | Brown et al. | |
| 8,765,485 B2 | 7/2014 | Link et al. | |
| 9,150,852 B2 | 10/2015 | Samuels et al. | |
| 10,161,007 B2 | 12/2018 | Abate et al. | |
| 2003/0156993 A1 | 8/2003 | Staats | |
| 2004/0253613 A1* | 12/2004 | Taylor | B01J 19/0046 435/6.11 |
| 2005/0019902 A1 | 1/2005 | Mathis et al. | |
| 2005/0112639 A1 | 5/2005 | Wang et al. | |
| 2007/0039866 A1 | 2/2007 | Schroeder et al. | |
| 2007/0077572 A1 | 4/2007 | Tawfik et al. | |
| 2007/0141593 A1 | 6/2007 | Lee et al. | |
| 2007/0231880 A1 | 10/2007 | Chang-Yen et al. | |
| 2008/0014589 A1 | 1/2008 | Link et al. | |
| 2009/0045064 A1 | 2/2009 | Simmons et al. | |
| 2009/0098555 A1 | 4/2009 | Roth et al. | |
| 2010/0015614 A1 | 1/2010 | Beer et al. | |
| 2010/0028915 A1 | 2/2010 | Gualberto et al. | |
| 2010/0055677 A1 | 3/2010 | Colston, Jr. et al. | |
| 2010/0173394 A1 | 7/2010 | Colston, Jr. et al. | |
| 2010/0285975 A1 | 11/2010 | Mathis et al. | |
| 2011/0053798 A1 | 3/2011 | Hindson et al. | |
| 2011/0056575 A1 | 3/2011 | Hong et al. | |
| 2011/0059556 A1 | 3/2011 | Strey et al. | |
| 2011/0103176 A1 | 5/2011 | Van Dam et al. | |
| 2011/0104816 A1 | 5/2011 | Pollack et al. | |
| 2011/0118151 A1 | 5/2011 | Eshoo et al. | |
| 2011/0160078 A1 | 6/2011 | Fodor et al. | |
| 2011/0217736 A1 | 9/2011 | Hindson et al. | |
| 2011/0311978 A1 | 12/2011 | Makarewicz et al. | |
| 2012/0010086 A1 | 1/2012 | Froehlich et al. | |
| 2012/0045765 A1 | 2/2012 | Curran et al. | |
| 2012/0122714 A1 | 5/2012 | Samuels et al. | |
| 2012/0309002 A1 | 6/2012 | Link | |
| 2012/0190032 A1 | 7/2012 | Ness et al. | |
| 2012/0190033 A1 | 7/2012 | Ness et al. | |
| 2012/0196288 A1 | 8/2012 | Beer | |
| 2012/0219947 A1 | 8/2012 | Yurkovetsky et al. | |
| 2012/0220494 A1 | 8/2012 | Samuels et al. | |

(Continued)

FOREIGN PATENT DOCUMENTS

AU 2013203624 A1 5/2013
DE 10339452 A1 3/2005
(Continued)

OTHER PUBLICATIONS

International Search Report and Written Opinion received for International Application No. PCT/US2018/057410, dated Feb. 8, 2019, 14 pages.
Pellegrino, et al., "High-Throughput Single-Cell DNA sequencing of AML Tumors with Droplet Microfluidics," bioRxiv preprint posted online, Oct. 13, 2017, 21 pages, http://dx.doi.org/10.1101/203158.
Lan, et al., "Single-Cell Genome Sequencing at Ultra-High-Throughput with Microfluidic Droplet Barcoding," journal, Jul. 2017, pp. 640-646, vol. 35, No. 7, Nature Biotechnology.
Zeng, et al., "High Performance Single Cell Genetic Analysis Using Microfludic Emulsion Generator Arrays," journal, Apr. 15, 2010, pp. 3138-3190, vol. 82, No. 8, Analytical Chemistry.

(Continued)

*Primary Examiner* — Tracy Vivlemore
*Assistant Examiner* — Sahana S Kaup
(74) *Attorney, Agent, or Firm* — Spectrum IP Law Group LLC

(57) ABSTRACT

The disclosed embodiments relate to method, apparatus and system for high throughput single-cell DNA sequencing with droplet microfluidic. In an exemplary embodiment, a method for analyzing nucleic acids within a cell includes the steps of: (a) flowing individual cells together with a material capable of forming a polymer or microsphere that retains nucleic acids into a carrier fluid such that droplets are formed; (b) breaking the emulsion and collecting the microsphere hydrogels in an aqueous fluid; and (c) performing combinatorial labeling on the nucleic acids contained within the microspheres/hydrogels.

6 Claims, 25 Drawing Sheets

(56) References Cited

U.S. PATENT DOCUMENTS

| | | |
|---|---|---|
| 2012/0258870 A1 | 10/2012 | Schwartz et al. |
| 2012/0264646 A1 | 10/2012 | Link et al. |
| 2012/0316074 A1 | 12/2012 | Saxonov et al. |
| 2013/0032235 A1 | 2/2013 | Johnstone et al. |
| 2013/0084572 A1 | 4/2013 | Hindson et al. |
| 2013/0095469 A1 | 4/2013 | Koltay et al. |
| 2013/0116130 A1 | 5/2013 | Fu et al. |
| 2013/0130919 A1 | 5/2013 | Chen et al. |
| 2013/0189700 A1 | 7/2013 | So et al. |
| 2013/0203605 A1 | 8/2013 | Shendure et al. |
| 2013/0210639 A1 | 8/2013 | Link et al. |
| 2013/0236901 A1 | 9/2013 | Potier et al. |
| 2014/0057799 A1 | 2/2014 | Johnson et al. |
| 2014/0154695 A1 | 6/2014 | Miller et al. |
| 2014/0155295 A1 | 6/2014 | Hindson et al. |
| 2014/0179544 A1 | 6/2014 | Steenblock et al. |
| 2014/0199731 A1 | 7/2014 | Agresti et al. |
| 2014/0272988 A1 | 9/2014 | Zador et al. |
| 2014/0323316 A1 | 10/2014 | Drmanac et al. |
| 2014/0378349 A1 | 12/2014 | Hindson et al. |
| 2015/0232942 A1 | 5/2015 | Abate et al. |
| 2015/0298091 A1 | 10/2015 | Weitz et al. |
| 2015/0376609 A1* | 12/2015 | Hindson ............ C12N 15/1065 506/4 |
| 2016/0177375 A1 | 6/2016 | Abate et al. |
| 2017/0009275 A1 | 1/2017 | Abate et al. |
| 2017/0022538 A1 | 1/2017 | Abate et al. |
| 2017/0121756 A1 | 5/2017 | Abate et al. |
| 2018/0056288 A1 | 3/2018 | Abate et al. |
| 2018/0216160 A1 | 8/2018 | Abate et al. |
| 2018/0237836 A1 | 8/2018 | Abate et al. |

FOREIGN PATENT DOCUMENTS

| | | |
|---|---|---|
| EP | 1547677 A1 | 6/2005 |
| EP | 2145955 A2 | 2/2012 |
| WO | 9412216 A1 | 6/1994 |
| WO | 2007140015 A2 | 12/2007 |
| WO | 2009050512 A2 | 4/2009 |
| WO | 2009054870 A2 | 4/2009 |
| WO | 2009111014 A2 | 9/2009 |
| WO | 2010148039 A2 | 12/2010 |
| WO | 2011047307 A2 | 4/2011 |
| WO | 2012011091 A2 | 1/2012 |
| WO | 2012048341 A1 | 4/2012 |
| WO | 2012162267 A2 | 5/2012 |
| WO | 2012083225 A2 | 6/2012 |
| WO | 2012109600 A2 | 8/2012 |
| WO | 2012142213 A2 | 10/2012 |
| WO | 2013119753 A1 | 8/2013 |
| WO | 2013126741 A2 | 8/2013 |
| WO | 2013130512 A2 | 9/2013 |
| WO | 2013134261 A1 | 9/2013 |
| WO | 2013173394 A2 | 11/2013 |
| WO | 2014028378 A2 | 2/2014 |
| WO | 2014028537 A2 | 2/2014 |
| WO | 2014047556 A2 | 3/2014 |
| WO | 2014083435 A2 | 6/2014 |
| WO | 2014093676 A2 | 6/2014 |
| WO | 2014108323 A1 | 7/2014 |
| WO | 2014138132 A2 | 9/2014 |
| WO | 2014151658 A2 | 9/2014 |
| WO | 2014153071 A1 | 9/2014 |
| WO | 2015120398 A2 | 2/2015 |
| WO | 2015031691 A1 | 3/2015 |
| WO | 2015200717 A2 | 6/2015 |
| WO | 2015157369 A1 | 10/2015 |
| WO | 2016/065056 A1 | 4/2016 |
| WO | 2016064755 A2 | 4/2016 |
| WO | 2016/126871 A2 | 8/2016 |
| WO | 2016126865 A1 | 8/2016 |

OTHER PUBLICATIONS

International Search Report and Written Opinion received for International Application No. PCT/US2018/056575, dated Jan. 3, 2019, 15 pages.

Eastburn, et al., "Microfluidic Droplet Enrichment for Targeted Sequencing," journal, Apr. 14, 2015, pp. 1-8, vol. 43, Nucleic Acids Research.

Sukovich, et al., "Bulk Double Emulsification for Flow Cytometric Analysis of Microfluidic Froplets," journal, Nov. 13, 2017, 5 pages, DOI:10.1039/c7an01695f, Royal Society of Chemistry.

Hunt JA, et al; (1994) "Effect of pH on the stability and surface composition of emulsions made with whey protein isolate"; Journal of Agricultural and Food Chemistry.;42(10); pp. 2131-2135.

Huston et al; (1988) "Protein engineering of antibody binding sites: recovery of specific activity in an anti-digoxin single-chain Fv analogue produced in *Escherichia coli*"; Proc. Nal Acad. Sci. U.S.A., 85; pp. 5879-5883.

International search report and written opinion dated Feb. 21, 2014 for PCT/US2013/054517.

Kawasaki, "Sample Preparation From Blood, Cells, and Other Fluids," Book, 1990, Chapter 18 pp. 146-152, PCR Protocols: A Guide to Methods and Applications.

Ki, JS., et al. (2005) "Integrated method for single-cell DNA extraction, PCR amplification, and sequencing of ribosomal DNA from harmful Dinoflagellates Cochlodium polykrikoides and Alexandrium catenella"; Marine Biotechnology, vol. 6; pp. 587-593.

Kiss MM, et al.(2008) "High-Throughput Quantitative Polymerase Chain Reaction in Picoliter Droplets"; Anal Chem 80(23); pp. 8975-8981.

Kritikou Ekat; "It's cheaper in the Picolab"; Nat Rev Genet, 6; (Sep. 2005); pp. 668.

Lagally ET, et al; (2001) "Single-Molecule DNA Amplification and Analysis in an Integrated Microfluidic Device"; Analytical Chemistry.;73(3); pp. 565-570.

Lanza Vecchia et al; (1987) "The use of hybrid hybridomas to target human cytotoxic T lymphocytes"; Eur. J. Immunol. 17(1); pp. 105-111.

Leary JF. (1994) "Strategies for rare cell detection and isolation"; Methods Cell Biol.;42(Pt B); pp. 331-358.

Lim, Shuan and Abate Adam, (2013) "Ultrahigh-throughput sorting of microfluidic drops with flow cytometry"; Lab Chip13; pp. 4563-4572.

Link, et al; (2004) "Geometrically mediated breaknp of drops in microfluidic devices"; Phys Rev Lett. 92(5):054503.

Livak KJ and Schmittgen TD; (2001) "Analysis of Relative Gene Expression Data Using Real-Time Quantitative PCR and the $2^{-\Delta\Delta CT}$ Method"; methods.;25(4); pp. 402-408.

Longo MC, et al; (1990) "Use of uracil DNA glycosylase to control carry-over contamination in polymerase chain reactions"; Gene.;93(1); pp. 125-128.

Malloggi F, et al; "Electrowetting-controlled droplet generation in a microfluidic flow-focusing device"; J. Phys.: Condens. Matter 19; (2007); 462101; 7 pages.

Markou Athina,et al; (2011) "Molecular Characterization of Circulating Tumor Cells in Breast Cancer by a Liquid Bead Array Hybridization Assay"; Clinical Chemistry 57:3; pp. 421-430.

Marcus et al., "Parallel Picoliter RT-PCR Assays Using Microfluidics"; Analytical Chemistry, 78(3); (2006); pp. 956-958.

Mary P Pascaline, et al; "Controlling droplet incubation using close-packed plug flow"; Biomicrojluidics 5; (2011); pp. 024101-1-024101-6.

Mazutis L, et al; (2013) "Single-cell analysis and sorting using droplet-based microfluidics"; Nature protocols.8(5); pp. 870-891.

McDonald, et al; (2000) "Fabrication of microfluidic systems in poly( dimethylsiloxane"; Electrophoresis, 21 (I); pp. 27-40.

Medkov A, Martina et al; "Analyzing Cancer at Single Cell Resolution with Droplet Technology"; American Association of Cancer Research (AACR); Apr. 19, 2010; 1 page.

(56) References Cited

OTHER PUBLICATIONS

Metzker, Michael L. "Sequencing technologies—the next generation"; Nature Reviews Genetics, vol. 11 (Jan. 2010); pp. 31-46.
Miyazaki, K; (2002) "Random DNA fragmentation with endonuclease V: application to DNA shuffling"; Nucleic Acids Res. 30(24); e139.
Miyazaki et al. (2013) "A new large-DNA-fragment delivery system based on integrase activity from an integrative and conjugative element"; Appl Environ Microbiol 79(14); pp. 4440-4447.
Moon Sangjun, et al; "Drop-on-Demand Single Cell Isolation and Total RNA Analysis"; PloS ONE, vol. 6, Issue 3; e17455 (Mar. 2011); pp. 1-10.
Morton et al; (2008) "Crossing microfluidic streamlines to lyse, label and wash cellst"; Lab on a Chip, 8(9); pp. 1448-1453.
Mui B, et al; (1993) "Osmotic properties oflarge unilamellar vesicles prepared by extrusion"; Biophysical journal 64(2); pp. 443-453.
Nagrath Sunitha, et al; "Isolation of rare circulating tumour cells in cancer patients by microchip technology"; Nature 450(7173); Dec. 20; 2007; pp. 1235-1239.
Nakano M, et al. (2005) "Single-molecule reverse transcription polymerase chain reaction using water-in-oil emulsion"; J Biosci Bioeng 99; pp. 293-295.
Nikolova AN and Jones MN; (1996) "Effect of grafted PEG-2000 on the size and permeability of vesicles"; Biochimica et Biophysica Ada (BBA)—Lipids and Lipid Metabolism.; 1304(2); pp. 120-128.
Nishikawa, Yohei et al (2015) "Monodisperse Picoliter Droplets for Low-Bias and Contamination-Free Reactions in Single-Cell Whole Genome Amplification" PLoS One 10(9); pp. e0138733.
Novak, et al; (2011) "Single-cell multiplex gene detection and sequencing with microfluidically generated agarose emulsions"; Angew Chem Int Ed Engl. 50(2):390-395.
Nunes, et al. "Dripping and Jelling in Microfluidic Multiphase Flows Applied to Particle and Fiber Synthesis," Journal, 2013, 46(11), J Phys D Appl Phys, pii 114002.
Oberholzer,Thomas, et al; (1995) "Polymerase chain reaction in liposomes"; Chemistry & Biology vol. 2 No. 10; pp. 677-682.
O'Donovan B, et al; (2012) "Electrode-free picoinjection of microfluidic drops"; Lab Chip 12; pp. 4029-4032.
Okochi M et al; (2010) "Droplet-based gene expression analysis using a device with magnetic force-based-droplet-handling system"; J Biosci Bioeng. 109(2); pp. 193-197.
Perry DJ; (1999) "Solid-Phase Sequencing of Biotinylated PCR Products with Streptavidin-Coated Magnetic Beads"; Hemostasis and Thrombosis Protocols: Springer;. p. 49-54.
Piatek AS, et al; (1998) "Molecular beacon sequence analysis for detecting drug resistance in *Mycobacterium tuberculosis*";. Nat Biotechnol.16(4); pp. 359-363.
Priest Craig, et al; (2006) "Controlled electrocoalescence in microfluidics: Targeting a single lamella"; Appl Phys Lett, 89; pp. 134101-1-134101-3.
Rolando, et al. "Cell Host & Microbe," 2013, pp. 395-405, 13.4.
Sciambia Adam and Abate Adam R., (2015) "Accurate microfluidic sorting of droplets at 30 kHz"; Lab Chip 15(1); pp. 47-51.
Sciambi et al. (2013) "Adding reagent to droplets with controlled rupture of encapsulated double emulsions"; Biomicrofluidics 7(4); pp. 1-6.
Scotts. H, et al; (2011) "Microfluidic immunomagnetic multi-target sorting—a model for controlling deflection of paramagnetic beads"; Lab Chip 11; pp. 2577-2582.
Seemann R, et al; (2012) "Droplet based microfluidics"; Rep Prag Phys 75; pp. 016601.
Shui et al; (2011) "Microfluidic DNA fragmentation for on-chip genomic analysis" Nanotechnology 22(49): 494013. 7 pages.
Sidore, et al (2016) "Enhanced sequencing coverage with digital droplet multiple displacement amplification"; Nuclei. Acids Res. 44(7):e66.; pp. 1-9.
Siegel Adam C,et al; (2007) "Microsolidics: Fabrication of Three-Dimensional Metallic Microstructures in Poly ( dimethy lsiloxane )"; Adv Mater 19; pp. 727-733.
Song H, et al; (2006) "Reactions in droplets in microfluidic charmels" Angew Chem Int Ed Engl 45; pp. 7336-7356.

Squires Tom M.; "Microfluidics: Fluid physics at the nanoliter scale"; Reviews of modem physics.;77(3); (Jul. 2005) pp. 977-1026.
Stone HA, et al; (2004) "Engineering flows in small devices: microfluidics toward a lab-on-a-chip"; Annu Rev Fluid Mech.;36; pp. 381-411.
Stott Shannon L; et al; "Isolation of circulating tumor cells using a microvortex-generating herringbone-chip"; PNAS vol. 107, No. 43; Oct. 26, 2010; pp. 18392-18397.
Syed et al. (2009) "Next-generation sequencing library preparation: simultaneous fragmentation and tagging using in vitro transposition"; Nature Methods vol. 6; pp. 1-2.
Tadmor AD, et al; (2011) "Probing individual enviromnental bacteria for viruses by using microfluidic digital PCR"; Science.;333(6038); pp. 58-62.
Takagi et al. (2005) "Continuous particle separation in a microchannel having asymmetrically arranged multiple branches" Lab Chip, 5(7); pp. 778-784.
Tamminen, et al. "Single Gene-Based Distinction of Individual Microbial Genomes from a Mixed Population of Microbial Cells," Journal, 2015, pp. 1-10, 6:195, Front Microbiol.
Teh SY,et al; "Droplet microfluidics"; Lab Chip 8; (2008); pp. 198-220.
Tewhey Ryan, et al; "Microdroplet-based PCR enrichment for large-scale targeted sequencing"; Nature Biotechnology, vol. 27 No. II; (Nov. 2009); pp. 1025-1035.
Thomann Y, et al; (2005) "PMMA Gradient Materials and in situ Nanocoating via Self-Assembly ofSemifluorinated Hyperbranched Amphiphiles"; Macromolecular Chemistry and Physics.;206(1); pp. 135-141.
Thorsen T, et al; (2001) "Dynamic pattern formation in a vesicle-generating microfluidic device"; Phys Rev Lett 86; pp. 4163-4166.
Tsai Scott S. H., et al; (2011) "Microfluidic immunomagnetic multi-target sorting—a model for controlling deflection of paramagnetic beads"; Lab Chip 11; pp. 2577-2582.
Ullal, et al; (2014) "Cancer cell profiling by barcoding allows multiplexed protein analysis in fine needle aspirates"; Sci Transl Med. 6(219):219ra9; pp. 1-22.
Utada, et al; (2007) "Dripping to jetting transitions in co flowing liquid streams"; Phys Rev Lett. Aug. 31, 2007;99(9; pp. 094502-1-094502-4.
Vanapalli SA,et al; "Hydrodynamic resistance of single confined moving drops in rectangular microchannels"; Lab Chip 9 (2009); pp. 982-990.
Vickers, et al., (2006) "Generation of Hydrophilic Poly(dimethylsiloxane) for High-Performance Microchip Electrophoresis"; Anal. Chem, 78(21); pp. 7446-7452.
Wang C, et al; (2012) "Amphiphilic building blocks for self-assembly: from amphiphiles to supra-amphiphiles"; Accounts of Chemical Research 45(4); pp. 608-618.
Wheeler et al, (2005) "Digital microfluidics with in-line sample purification for proteomics analyses with MALDI-MS"; Anal Chem. 77(2); 534-540.
Whitcombe D, et al; (1999) "Detection of PCR products using self-probing amplicons and fluorescence"; Nature biotechnology 17(8); pp. 804-807.
Whitesides GM. (2006) The origins and the future ofmicrofluidics. Nature 442(7101); pp. 368-373.
Xia YN, et al; (1998) "Soft lithography"; Angew Chem Int Edit 37; pp. 551-575.
Yu, et al (2014) "Mung bean nuclease treatment increases capture specificity of microdroplet-PCR based targeted DNA enrichment"; PLoS One 9(7):e103491; pp. 1-7.
Zheng, B, et al; (2004) "Formation of droplets of in microfluidic channels alternating composition and applications to indexing of concentrations in droplet-based assays"; Anal Chem 76; pp. 4977-4982.
Zhong Qun, et al; (2011) "Multiplex digital PCR: breaking the one target per color barrier of quantitative PCR"; Lab Chip 11; pp. 2167-2174.
Zhu, et al., "Highly Sensitive and Quantitative Detection of Rare Pathogens Through Agarose Droplet Microfluidic Emulsion PCR at the Single-Cell Level," Journal, 2012, pp. 3907-3913, 12(20), Lab on a Chip.

(56) References Cited

OTHER PUBLICATIONS

Zhu et al., (2001) "Reverse transcriptase template switching: a SMART approach for full-length cDNA library construction"; BioTechniques 30: pp. 892-897.
Zien TF; (1969) "Hydrodynamics of bolus flow—an analytical approach to blood flow in capillaries"; Math Biophys, 31; pp. 681-694.
Kuster, et al., "Interfacing Droplet Microfluidics with Matrix-Assisted Laser Desorption/Ionization Mass Spectrometry: Label-Free Content Analysis of Single Droplets," Analytical Chemistry, 2013, pp. 1285-1289, 85, ACS Publications.
Abate, et al., "Microfluidic Sorting With High-Speed Single-Layer Membrane Valves," Journal, 2010, pp. 203509-1-203509-3, Applied Physics Letters 96.
Abate, et al., "High-Throughput Injection With Microfluidics Using Picoinjectors," Journal, Nov. 9, 2010, pp. 19163-19166, vol. 107 1 No. 45, PNAS.
Abate, et al., "Efficient Encapsulation With Plug-Triggered Drop Formation," Journal, 2011, 84(3):031502, Physical Review E.
Abate, et al., "Faster Multiple Emulsification with Drop Splitting," Journal 2011, pp. 1911-1915, 11(11), Lab on a Chip.
Abate, et al., "One-Step Formation of Multiple Emulsions in Microfluidics," Journal, 2011, pp. 253-258, 11(2), Lab on a Chip.
Abate, et al., "Photoreactive Coating for High-Contrast Spatial Patterning of Microfluidic Device Wettability," Journal, 2008, pp. 2157-2160, 8(12), Lab on a Chip.
Agresti, et al., "Ultrahigh-Throughput Screening in Drop-Based Microfluidics for Firected Evolution," Journal, 2008, pp. 4004-4009, vol. 107, No. 9, PNAS.
Agresti, et al., "Ucorrection for Ultrahigh-throughput Screening in Drop-Based Microfluidics for Directed Evolution," Journal, 2010, pp. 6550-6551, 107, Proc. Natl Acad Sci., US.
Ahn, et al., "Electrocoalescence of Drops Synchronized by Size-Dependent Flow in Microfluidic Channels," Journal, 2006, pp. 264105-1-264105-3, Appl Phys Lett 88.
Ali, et al., "Rolling Circle Amplification: a Versatile Tool for Chemical Biology, Materials Science and Medicine," Journal, Mar. 18, 2017, pp. 3324-3341, vol. 43, Chem Soc Rev.
Allen, et al., "Single Virus Genomics: A New Tool for Virus Discovery," Journal, 2011, 6(3):e17722, PLoS One.
Arriaga, et al. "Ultrathin Shell Double Emulsion Templated Giant Unilamellar Lipid Vesicles With Controlled Microdomain Formations," Journal, 2014, pp. 950-956, 10(5), Small.
Atten, "Electrocoalescence of Water Droplets in an Insulating Liquid" Journal, 1993, pp. 259-569, J Electrostat 30.
Barenholz, et al. "A Simple Method for the Preparation of Homogeneous Phospholipid Vesicles" Journal, 1977, pp. 2806-2810, 12(12), Biochemistry.
Baret, et al. "Fluorescence-activated Droplet Sorting (FADS): Efficient Microfluidic Cell Sorting Based on Enzymatic Activitys," Journal, 2009, pp. 1850-1858, 9(13), Lab on a Chip.
Battaglia, et al. "Polymeric Vesicle Permeability: A Facile Chemical Assay" Journal, 2006, pp. 4910-4913, 22(11), Langmuir.
Beer, et al. "On-Chip Single-Copy Real-0Time Reverse-Transcription PCR in Isolated Picoliter Droplets" Journal, 2008, pp. 1854-1858, Anal Chem 80.
Bernath, et al., "In Vitro Compartmentalization by Double Emulsions: Sorting and Gene Enrichment by Fluorescence Activated Cell Sorting" Journal, 2004, pp. 151-157, Analytical Biochemistry 325.
Bird, et al. "Single-Chain Antigen-Binding Proteins" Journal, 1988, pp. 423-426, Science 242.
Blainey PC "The Future is Now: Single-Cell Genomics of Bacteria and Archaea" Journal, 2013, pp. 407-427, 37(3), FEMS Microbiology Reviews.
Brouzes, et al., "Droplet Microfluidic Technology for Single-Cell High-Throughput Screening," Journal, Aug. 25, 2009, pp. 14195-14200, vol. 106 No. 34, PNAS.
Brown, et al., "Current Techniques for Single-Cell Lysis" Journal, 2008, pp. S131-S138, J.R. Soc. Interface 5.
Caron, "Assessment of Bacterial Viabiligy Status by Flow Cytometry and Single Cell Sorting," Journal, 1998, pp. 988-998, 84(6), Journal of Applied Microbiology.
Chaffer, et al., "A Perspective on Cancer Cell Metastasis" Journal, Mar. 25, 2011, pp. 1559-1564, vol. 331, Science.
Chabert, et al. "Droplet Fusion by Alternating Current (AC) Field Electrocoalesence in Microchannels" Journal, 2005 pp. 3706-3715, Electrophoresis 26.
Chen, et al. "Influence of pH on the Stability of Oil-In-Water Emulsions Stabilized by a Splittable Surfactant," Journal, 2000, pp. 173-179, 170(2), Colloids and Surfaces A: Physicochemical and Engineering Aspects.
Chung, et al., "Droplet Dynamics Passing Through Obstructions in Confined Microchannel Flow," Journal, 2010, pp. 1151-1163, 9(6), Microfluidics Nanofluidics.
Clausell-Tormos, et al., "Droplet-Based Microfluidic Platforms for the Encapsulation and Screening of Mammalian Cells and Multicellular Organismsm" Journal, May 2008, pp. 427-437, Chemistry and Biology 15.
Dejournette CJ, et al; (2013) "Creating Biocompatible Oil-Water Interfaces without Synthesis: Direct Interactions between Primary Amines and Carboxylated Perfluorocarbon Surfactants"; Analytical chemistry.;85(21); pp. 10556-10564.
Dietrich et al; "Effects of UV irradiation and hydrogen peroxide on DNA fragmentation, motility and fertilizing ability of rainbow trout (Oncorhynchus mykiss) spermatozoa"; Theriogenology. vol. 64; (Nov. 2005) pp. 1809-1822.
Duffy DC, et al; (1998) "Rapid Prototyping ofMicrofluidic Systems in Poly(dimethylsiloxane)"; Anal. Chem. 70; pp. 4974-4984.
Eastburn Dennis J., et al; (2013) "Ultrahigh-Throughput Mammalian Single-Cell Reverse-Transcriptase Polymerase Chain Reaction in Microfluidic Drops"; Anal. Chem. 85; pp. 8016-8021.
Eastburn DJ,et al; (2013) "Picoinjection Enables Digital Detection of RNA with Droplet RT-PCR"; PloS one.;8(4): e62961.
Edd et al., (2008) Controlled encapsulation of single cells into monodisperse picoliter drop Lab on a Chip, 8(8); pp. 1262-1264.
European search report and opinion dated Feb. 8, 2016 for EP Application No. 13829925.
Frenz L, et al; (2009) "Reliable microfluidic on-chip incubation of droplets in delay-lines"; Lab on a Chip 9(10); pp. 1344-1348.
Fu, Yusi et al (2015) "Uniform and accurate single-cell sequencing based on emulsion whole-genome amplification"; Proc Natl Acad Sci US A. 112(38); pp. 11923-11928.
Garstecki P. et al; "Formation of droplets and bubbles in a microfluidic T-junction-scaling and mechanism of break-up"; Lab Chip 6; (2006); pp. 437-446.
Gevensleben H, et al; (2013) "Noninvasive Detection ofHER2 Amplification with Plasma DNA Digital PCR"; Clinical Cancer Research.;19(12); pp. 3276-3284.
Gribskov, et al; (1986) "Sigma factors from *E. coli, B. subtilis*, phage SP01, and phage T4 are homologous proteins"; Nucl. Acids Res. 14(6):6745-6763.
Grover, et al. "Multiple Displacement Amplification as a pre-Polymerase Chain Reaction (pre-PCR) to Detect Ultra Low Population of Ralstonia Solanacearum (Smith 1896) Yabuchi et al. (1996)" Journal, 2009, pp. 539-543, 49(5), Lett Appl Microbiol.
Hayward RC, et al; (2006) "Dewetting instability during the formation of polymersomes from block-copolymer-stabilized double emulsions"; Langmuir 22(10); pp. 4457-4461.
Herminghaus S, "Dynamical Instability of Thin Liquid Films Between Conducting Media"; Physical Review Letter, vol. 83, No. 12; Sep. 20, 1999; pp. 2359-2361.
Holland, et al; (1991) "Detection of specific polymerase chain reaction product by utilizing the 5'-3' exonuclease activity of Thermus aquaticus DNA polymerase"; PNAS, 88 (16); 7276-7280.
Holtyze C., et al; (2008) "Biocompatible surfactants for water-in-fluorocarbon emulsions"; Lab Chip 8; pp. 1632-1639.
Horton et al; "Gene splicing by overlap extension: tailor-made genes using the polymerase chain reaction"; Biotechniques, vol. 54; Mar. 1, 2013; pp. 129-133.
Hu, Hoa et al; (2009) "Mutation screening in 86 known X-linked mental retardation genes by droplet-based multiplex PCR and massive parallel sequencing"; HUGO J.3; pp. 41-49.

(56) References Cited

OTHER PUBLICATIONS

Huebner, et al; (2008) "Microdroplets: A sea of applications?"; Lab on a Chip, 8; pp. 1244-1254.
Hunkapiller and Hood, (1986) "Immunology: The Growing Immunoglobulin Gene Superfamily"; Nature, 323; pp. 15-16.

* cited by examiner

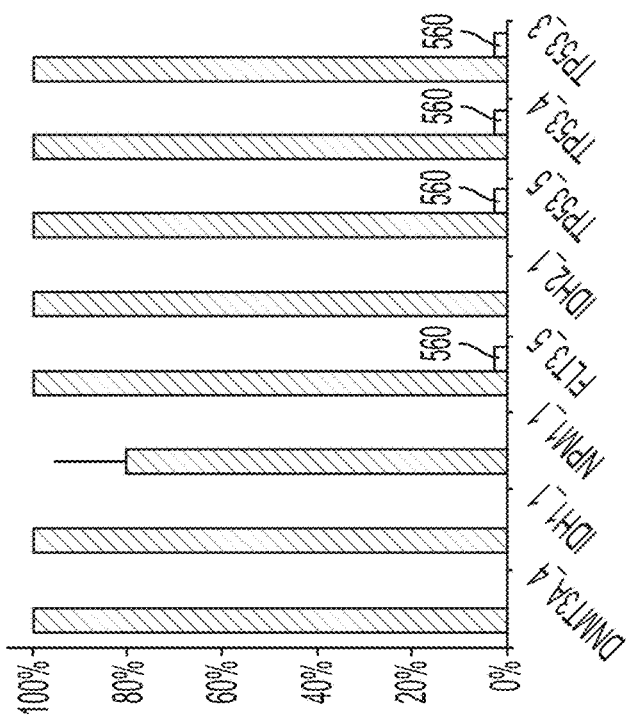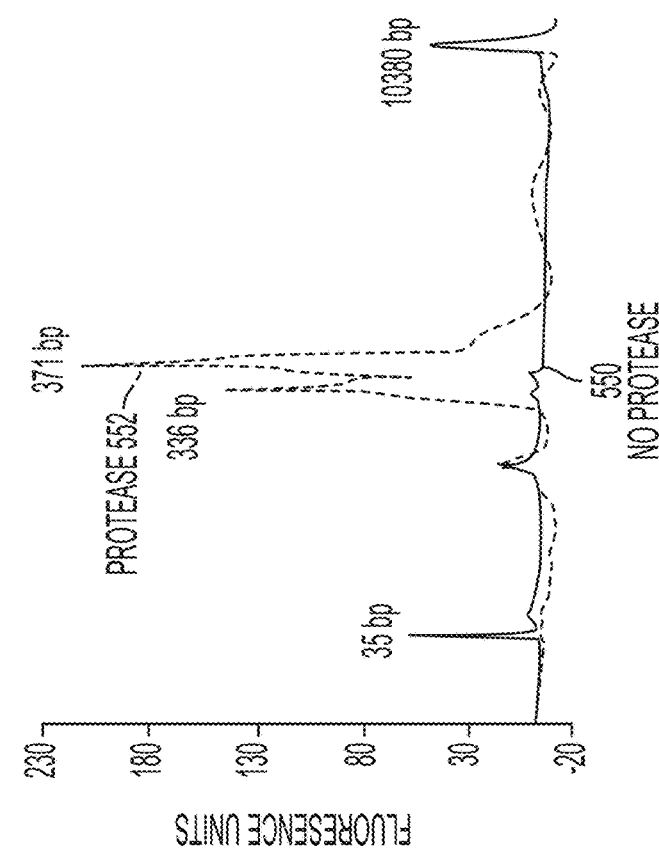
FIG. 5C

| CHROMOSOME | GENE | INSERT START | INSERT END | AMPLICON NAME |
|---|---|---|---|---|
| chr1 | NRAS | 115256325 | 115256546 | NRAS_1 |
| chr1 | NRAS | 115258554 | 115258776 | NRAS_2 |
| chr11 | WT1 | 32413416 | 32413641 | WT1_2 |
| chr11 | WT1 | 32414126 | 32414348 | WT1_1 |
| chr11 | WT1 | 32417766 | 32417992 | WT1_3 |
| chr11 | CBL | 119148819 | 119149034 | CBL_2 |
| chr11 | CBL | 119149210 | 119149431 | CBL_1 |
| chr12 | KRAS | 25380260 | 25380466 | KRAS_2 |
| chr12 | KRAS | 25398184 | 25398405 | KRAS_1 |
| chr12 | KRAS | 25378550 | 25378658 | KRAS_3 |
| chr12 | PTPN11 | 112888117 | 112888327 | PTPN11_2 |
| chr12 | PTPN11 | 112926780 | 112926999 | PTPN11_1 |
| chr13 | FLT3 | 28592495 | 28592723 | FLT3_1 |
| chr13 | FLT3 | 28602180 | 28602404 | FLT3_3 |
| chr13 | FLT3 | 28608138 | 28608361 | FLT3_2 |
| chr13 | FLT3 | 28609548 | 28609769 | FLT3_4 |
| chr15 | IDH2 | 90631735 | 90631962 | IDH2_1 |
| chr17 | TP53 | 7576954 | 7577180 | TP53_4 |
| chr17 | TP53 | 7577398 | 7577615 | TP53_2 |
| chr17 | TP53 | 7578087 | 7578296 | TP53_1 |
| chr17 | TP53 | 7578385 | 7578605 | TP53_3 |

FIG. 6

| CHROMOSOME | GENE | INSERT START | INSERT END | AMPLICON NAME |
|---|---|---|---|---|
| chr17 | MIR142 | 56408608 | 56408751 | MIR142_1 |
| chr17 | SRSF2 | 74732883 | 74733050 | SRSF2_2 |
| chr2 | DNMT3A | 25457136 | 25457351 | DNMT3A_10 |
| chr2 | DNMT3A | 25458489 | 25458714 | DNMT3A_6 |
| chr2 | DNMT3A | 25461897 | 25462088 | DNMT3A_13 |
| chr2 | DNMT3A | 25463103 | 25463329 | DNMT3A_2 |
| chr2 | DNMT3A | 25463446 | 25463673 | DNMT3A_5 |
| chr2 | DNMT3A | 25466627 | 25466857 | DNMT3A_1 |
| chr2 | DNMT3A | 25470473 | 25470641 | DNMT3A_4 |
| chr2 | SF3B1 | 198266762 | 198266977 | SF3B1_1 |
| chr2 | SF3B1 | 198267157 | 198267384 | SF3B1_2 |
| chr2 | IDH1 | 209112899 | 209113123 | IDH1_1 |
| chr20 | ASXL1 | 31022370 | 31022586 | ASXL1_1 |
| chr20 | ASXL1 | 31022846 | 31023073 | ASXL1_2 |
| chr21 | RUNX1 | 36164786 | 36164997 | RUNX1_5 |
| chr21 | RUNX1 | 36171483 | 36171710 | RUNX1_2 |
| chr21 | RUNX1 | 36206706 | 36206884 | RUNX1_3 |
| chr21 | RUNX1 | 36231605 | 36231834 | RUNX1_4 |
| chr21 | RUNX1 | 36252812 | 36253007 | RUNX1_7 |
| chr21 | U2AF1 | 44514701 | 44514922 | U2AF1_1 |
| chr21 | U2AF1 | 44524280 | 44524505 | U2AF1_2 |

FIG. 6
CONTINUED

| CHROMOSOME | GENE | INSERT START | INSERT END | AMPLICON NAME |
|---|---|---|---|---|
| chr3 | GATA2 | 128202724 | 128202891 | GATA2_1 |
| chr4 | KIT | 55589608 | 55589829 | KIT_2 |
| chr4 | KIT | 55599232 | 55599448 | KIT_1 |
| chr4 | TET2 | 106156635 | 106156850 | TET2_15 |
| chr4 | TET2 | 106156867 | 106157094 | TET2_10 |
| chr4 | TET2 | 106157752 | 106157947 | TET2_13 |
| chr4 | TET2 | 106163914 | 106164128 | TET2_1 |
| chr4 | TET2 | 106164753 | 106164980 | TET2_6 |
| chr4 | TET2 | 106180645 | 106180865 | TET2_8 |
| chr4 | TET2 | 106182821 | 106183021 | TET2_5 |
| chr4 | TET2 | 106190719 | 106190932 | TET2_7 |
| chr4 | TET2 | 106196089 | 106196313 | TET2_3 |
| chr4 | TET2 | 106197100 | 106197318 | TET2_2 |
| chr5 | NPM1 | 170837502 | 170837616 | NPM1_1 |
| chr7 | EZH2 | 148504655 | 148504874 | EZH2_1 |
| chr7 | EZH2 | 148506333 | 148506547 | EZH2_2 |
| chr8 | RAD21 | 117878729 | 117878946 | RAD21_1 |
| chr9 | JAK2 | 5073564 | 5073785 | JAK2_1 |
| chrX | STAG2 | 123179102 | 123179318 | STAG2_1 |
| chrX | PHF6 | 133549083 | 133549301 | PHF6_1 |

FIG. 6
CONTINUED

| | DIAGNOSIS | REMISSION | RELAPSE |
|---|---|---|---|
| TOTAL READ PAIRS | 17,331,034 | 18,824,864 | 16,900,170 |
| READS MAPPING TO CELLS | 63% | 85% | 76% |
| TOTAL CELLS FOUND | 7,364 | 5,605 | 5,498 |
| AVERAGE READS PER CELL | 1,578 | 2,974 | 2,188 |
| NUMBER OF GENOTYPED CELLS | 4,748 | 4,384 | 4,236 |
| RAJI SPIKE IN DETECTION RATE | 1.0% | 1.3% | 4.8% |
| AVERAGE ALLELE DROPOUT RATE | 2.80% | 5.30% | 8.40% |

FIG. 7A

| GENE | TRANSCRIPT | STRAND | VARIANT COORDINATES (gDNA/cDNA/PROTEIN) | REGION |
|---|---|---|---|---|
| DNMT3A | NM_022552 | - | chr2:g.25457192G>A/c.2695C>T/p.R899C | cds_in_exon_23 |
| DNMT3A | NM_022552 | - | chr2:g.25458546C>T/c.2597+30G>A/. | intron_between_exon_22_and_23 |
| DNMT3A | NM_022552 | - | chr2:g.25463463G>A/c.2173+26C>T/. | intron_between_exon_18_and_19 |
| SF3B1 | NM_012433 | - | chr2:g.198266943C>T/c.2078-89G>A/. | intron_between_exon_14_and_15 |
| IDH1 | NM_001282387 | - | chr2:g.209113058delA/c.414+44delT/. | intron_between_exon_4_and_5 |
| KIT | NM_000222 | + | chr4:g.55599438T>C/c.2484+78T>C/. | intron_between_exon_17_and_18 |
| TET2 | NM_001127208 | + | chr4:g.106196092C>T/c.4538-113C>T/. | intron_between_exon_10_and_11 |
| NPM1 | NM_002520 | + | chr5:g.170837526delT/c.847-5delT/. | intron_between_exon_10_and_11 |
| EZH2 | NM_001203247 | - | chr7:g.148504722delTG/c.2241+21delG/. | 3'-UTR, noncoding_exon_20 |
| EZH2 | NM_001203247 | - | chr7:g.148504855_148504859dupGACTT/c.2181-61_2181-57dupAAGTC/. | intron_between_exon_19_and_20 |
| FLT3 | NM_004119 | - | chr13:g.28608255_28608275dupGATCATATTCATATATTCTCTGA / c.1784_1804dupGAGAATATGAATATGATCTCA/ p.R595_L601dupREYEVDL | cds_in_exon_14 |
| TP53 | NM_001126115 | - | chr17:g.7577180C>T/c.387-25G>A/. | intron_between_exon_3_and_4 |
| TP53 | NM_001126115 | - | chr17:g.7577407A>C/c.386+92T>G/. | intron_between_exon_3_and_4 |
| TP53 | NM_001126115 | - | chr17:g.7577427G>A/c.386+72C>T/. | intron_between_exon_3_and_4 |
| TP53 | NM_001126115 | - | chr17:g.7578115T>C/c.276+62A>G/. | intron_between_exon_2_and_3 |
| TP53 | NM_001126115 | - | chr17:g.7578394T>C/c.140A>G/p.H47R | cds_in_exon_1 |
| ASXL1 | NM_015338 | + | chr20:g.31022359T>C/c.2444T>C/p.L815P | cds_in_exon_12 |

FIG. 9

LIST OF 295 GENES TARGETED BY BULK SEQUENCING

| | | | | | | | | |
|---|---|---|---|---|---|---|---|---|
| CALR | CUL5 | FANCD2 | HIST1H2BF | LEF1 | NBN | PLA2G2D | SF3B1 | TINF2(TIN2) |
| CARD11 | CUX1 | FANCE | HIST1H3D | LRP1B | NCOR1 | PLCG2 | SFRS1 | TLR2 |
| CBL | CYLD | FANCG | HIST1H4D | LTB | NCOR2 | POT1 | SFRS7 | TLR9 |
| CBLB | DAXX | FANCI | HNRNPK | LUC7L2 | NF1 | POU2AF1 | SGK1 | TNFAIP3 |
| CCND1 | DCLRE1C | FANCL | HRAS | LYN | NFE2 | PRDM1 | SH2B3 | TNFRSF14 |
| CCND3 | DDX3X | FAS | ICOS | MALT1 | NFKB1 | PRKCB | SHH | TNKS |
| CD200 | DIS3 | FAT1 | ID3 | MAP2K1 | NFKB2 | PTEN | SMAD2 | TOX |
| CD274 | DKC1 | FAT3 | IDH1 | MAPK1 | NFKBIA | PTPN1 | SMC1A | TP53 |
| CD58 | DLC1 | FBXW7 | IDH2 | MAX | NFKBIE | PTPN11 | SMC3 | TRAF3 |
| CD79A | DNM2 | FGFR3 | IKBKA | MDM2 | NOTCH1 | RAD21 | SMC5 | TRAF6 |
| CD79B | DNMT1 | FLI1 | IKZF1 | MED12 | NOTCH2 | RAD51C | SNX7 | TYK2 |
| CDK4 | DNMT3A | FLT3 | IKZF2 | MEF2B | NPM1 | RAG1 | SOCS1 | TYK3 |
| CDKN2A | DNMT3B | FNDC3A | IKZF3 | MEF2C | NR3C2 | RAG2 | SOX5 | U2AF1 |
| CDKN2B | EBF1 | FOXP1 | IL7R | MGA | NRAS | RASA2 | SP140 | U2AF2 |
| CDKN2C | ECT2L | FYN | IRAK1 | miR125a | NSD2 | RB1 | SPEN | UBR5 |
| CEBPA | EED | G6PC3 | IRAK4 | miR-142 | NT5C2 | REL | SPIB | USP29 |
| CEBPE | EGR1 | GAB2 | IRF1 | miR155 | PAG1 | RELA | SRSF2 | VPREB1 |
| CHD2 | EGR2 | GATA1 | IRF4 | miR15a | PALB2 | RELB | STAG1 | WHSC1 |
| CHK2 | ELANE | GATA2 | IRF7 | miR16-1 | PAX5 | RELN | STAG2 | WHSC1L1 |
| CIITA | EP300 | GATA3 | ITPKB | MIR17HG | PDCD1 | RHOA | STAT1 | WT1 |
| CNOT3 | EPHA7 | GCET2 | JAK1 | miR21 | PDCD1LG2 | RIPK1 | STAT3 | XPO1 |
| CREBBP | EPOR | GFI1B | JAK2 | mir34b | PDGFRB | ROBO1 | SUZ12 | ZAP70 |
| CRLF2 | ERG | GNA13 | JAK3 | mir34c | PEG3 | ROR1 | SYK | ZMYM2 |
| CSF2RA | ETV6 | GNAS | JARID2 | MLL | PHF6 | RPL10 | TBL1XR1 | ZMYM3 |
| CSF3R | EZH2 | GNB1 | KDM4C | MLL2 | PHIP | RPL5 | TCF3 | ZRSR2 |
| CTBP1 | FAM46C | GPRC5A | KDM6A | MLL3 | PIGA | RUNX1 | TERC | |
| CTBP2 | FAM5C | HAX1 | KIT | MPL | PIK3CA | RUNX2 | TERT | |
| CTCF | FANCA | HIST1H1E | KLHL6 | MS4A1 | PIK3CB | SAMHD1 | TET1 | |
| CTLA4 | FANCB | HIST1H2AD | KRAS | MYB | PIK3CG | SETBP1 | TET2 | |
| CTNNA1 | FANCC | HIST1H2BE | LAMB4 | MYD88 | PIK3R1 | SETD2 | TGDS | |

FIG. 14

METHOD, SYSTEMS AND APPARATUS FOR SINGLE CELL ANALYSIS

The instant application is a continuation in part of U.S. application Ser. No. 16/164,595 (filed Oct. 18, 2018), which claimed priority to U.S. Provisional Application Nos. 62/574,103 (filed Oct. 18, 2017), 62/574,104 (filed Oct. 18, 2017) and 62/574,109 (filed Oct. 18, 2017). The instant application also claims priority to Provisional Application No. 62/576,455, filed Oct. 24, 2018. The specification of each of the foregoing applications is incorporated herein in its entirety.

BACKGROUND

The promise of precision medicine is to deliver highly targeted treatment to every single diseased cell. The conventional one-size-fits-all approach of medical treatments isn't working for many patients who need help. To move precision medicine forward, researchers and clinicians need to look at the origins of disease, the single cell, in new meaningful ways.

Because most diseases are not caused by just one mutation, understanding genetic variability, including mutation co-occurrence at the single-cell level, is vitally important for clinical researchers. This level of resolution is missed with existing bulk sequencing which can result in failed clinical trials, high costs, and poor patient outcomes. To impact precision drug discovery, development, and delivery, insight into the mutational differences within and among every single cell is needed.

The conventional technology for measuring cellular mutations and heterogeneity for complex disease is bulk sequencing based on averages. A problem with using averages is that the underlying genetic diversity is missed across cell populations. Understanding this diversity is important for patient stratification, therapy selection and disease monitoring. Moving beyond averages helps deliver on the promise of precision medicine.

Therefore, there is a need for method, system and apparatus to provide high-throughput, single-cell DNA sequencing.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 5C shows the NGC library yields and size distribution at 371 base pairs with and without protease from the sample of FIG. 5B.

FIG. 6 shows tabulated results of a variant allele information of a targeted panel according to an exemplary implementation of the disclosure.

FIG. 7A is a table displaying key metrics from the diagnosis, remission and relapse single cell DNA sequencing run from an AML patient.

FIG. 9 is a table showing 17 different variant alleles identified in the AML patient samples.

FIG. 14 is a table showing 295 genes that were targeted for bulk sequencing according to one embodiment of the disclosure.

DETAILED DESCRIPTION

Figure 1:
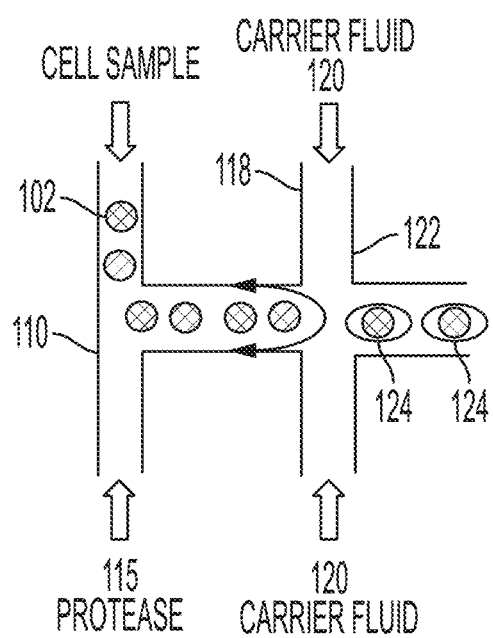
FIG. 1 schematically illustrates a portion of an exemplary platform for implementing a first step of forming cell droplets according to one embodiment of the disclosure.

Current tumor sequencing paradigms are inadequate to fully characterize many instances of AML (acute myeloid leukemia). A major challenge has been the unambiguous identification of potentially rare and genetically heterogeneous neoplastic cell populations with subclones capable of critically impacting tumor evolution and the acquisition of therapeutic resistance. Conventional bulk population sequencing is often unable to identify rare alleles or definitively determine whether mutations co-occur within the same cell. Single-cell sequencing has the potential to address these key issues and transform our ability to accurately characterize clonal heterogeneity in AML.

An established approach for high-throughput single-cell sequencing uses molecular barcodes to tag the nucleic acids of individual cells confined to emulsion droplets. Although it is now feasible to perform single-cell RNA sequencing on thousands of cells using this type of approach, high-throughput single-cell DNA genotyping using droplet microfluidics has not been demonstrated on eukaryotic cells. This is primarily due to the challenges associated with efficiently lysing cells, freeing genomic DNA from chromatin and enabling efficient PCR amplification in the presence of high concentrations of crude lysate.

To overcome these and other shortcoming of the conventional systems and to enable the characterization of genetic diversity within cancer cell populations, an embodiment of the disclosure provides a microfluidic droplet workflow that enables efficient and massively-parallel single-cell PCR-based barcoding. The microfluidic droplet workflow may be implemented in one or more steps on one or more instruments.

As stated, an embodiment of the disclosure provides a system and platform for scalable detection of genomic variability within and across cell populations. In one embodiment, the platform includes an instrument, consumables and software, which connect seamlessly into an existing Next-Generation Sequencing ("NGS") workflows. The disclosed platform provides a highly sensitive and customizable solution that is fully supported to enable biologically and clinically meaningful discoveries.

In one application of the disclosed embodiments, the platform utilizes a droplet microfluidic approach to identify heterogeneity in a population of at least 10,000 cells. Utilizing the disclosed droplet microfluidic embodiment allows rapid encapsulation, processing and profiling of thousands of individual cells for single-cell DNA applications. This enables accessing DNA for the detection of mutation co-occurrence at unprecedented scale. This approach also allows single nucleotide variant ("SNV") and indel detection while maintaining low allele dropout and high coverage uniformity as compared to the conventional methods requiring whole genome amplification. The disclosed embodiments are capable of working with customized content. Thus, the focus may remain on the targets of intertest that are most informative for disease detection and research. The ability to understand cellular heterogeneity at the single-cell level helps drive precision medicine.

FIG. 1 schematically a portion of an exemplary platform for implementing a first step of forming cell droplets according to one embodiment of the disclosure. Specifically, FIG. 1 shows, among others, the steps of cell encapsulation by partitioning cells into individual droplets and adding protease to the droplets. In FIG. 1, cell samples 102 are introduced into tubing system 110. Cells 102 my originate from a tumor. Cells 102 may be collected at different stages. For example, cells 102 may be collected at diagnosis, remission or relapse.

The cells may be extracted from biological samples. As used herein, the phrase biological sample encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term biological sample encompasses a clinical sample, and also includes cells in culture, cell supernatants, cell lysates, cells, serum, plasma, biological fluid, and tissue samples. Further, Biological sample may include cells; biological fluids such as blood, cerebrospinal fluid, semen, saliva, and the like; bile; bone marrow; skin (e.g., skin biopsy); and antibodies obtained from an individual.

In various aspects the subject methods may be used to detect a variety of components from such biological samples. Components of interest include, but are not necessarily limited to, cells (e.g., circulating cells and/or circulating tumor cells), polynucleotides (e.g., DNA and/or RNA), polypeptides (e.g., peptides and/or proteins), and many other components that may be present in a biological sample.

"Polynucleotides" or "oligonucleotides" as used herein refer to linear polymers of nucleotide monomers, and may be used interchangeably. Polynucleotides and oligonucleotides can have any of a variety of structural configurations, e.g., be single stranded, double stranded, or a combination of both, as well as having higher order intra- or intermolecular secondary/tertiary structures, e.g., hairpins, loops, triple stranded regions, etc. Polynucleotides typically range in size from a few monomeric units, e.g., 5-40, when they are usually referred to as "oligonucleotides," to several thousand monomeric units. Whenever a polynucleotide or oligonucleotide is represented by a sequence of letters (upper or lower case), such as "ATGCCTG", it will be understood that the nucleotides are in 5'.fwdarw.3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999).

The terms "polypeptide", "peptide", and "protein", used interchangeably herein, refer to a polymeric form of amino acids of any length. $NH_2$ refers to the free amino group present at the amino terminus of a polypeptide. COOH refers to the free carboxyl group present at the carboxyl terminus of a polypeptide. In keeping with standard polypeptide nomenclature, J. Biol. Chem., 243 (1969), 3552-3559 is used.

In certain aspects, methods are provided for counting and/or genotyping cells, including normal cells or tumor cells, such as CTCs. A feature of such methods is the use of microfluidics.

In some instances, cells 102 may comprise nucleic acids wherein the nucleic acids are from a tumor cell. In some instances, cells 102 may comprise a whole, intact cell. In some instances, droplet 102 may comprise a cell lysate. In some instances, a droplet comprises a partially lysed cell. In some instances, methods disclosed herein comprise lysing a cell before containing the nucleic acids thereof in a droplet.

In some instances, methods disclosed herein comprise lysing a cell after containing the nucleic acids thereof in a droplet. In some instances, methods comprise containing a cell and cell lysis reagents in a droplet. In some instances, methods comprise contacting a droplet with a cell lysis reagent. In some instances, methods comprise injecting a droplet with a cell lysis reagent. In some instances, methods comprise flowing droplets into a cell lysis reagent. In some instances, methods comprise flowing cell lysis reagent into a carrier fluid comprising droplets. In some instances, the lysis reagent comprises a detergent. In some instances, the lysis reagent comprises a protease. In some instances, the lysis reagent comprises a lysozyme. In some instances, the lysis reagent comprises a protease. In some instances, the lysis reagent comprises an alkaline buffer.

Encapsulating a component from a biological sample may be achieved by any convenient method. In one exemplary method, droplets are formed in a massively parallel fashion in a serial bisection device.

As shown in FIG. 1, protease 115 is introduced at a branch of tubing 110. Protease 115 may be used to solubilize cells 102. Protease 102 may comprise any conventional protease having one or more enzyme to perform proteolysis including protein catabolism by hydrolysis of peptide bonds.

At inlet 118, carrier fluid 120 is added to the mixture of cells 102 in protease 115. Adding carrier fluid 120 causes formation of droplets 124. Droplets 124 may generally contain cell 102 and protease 115. Droplets 124 are suspended in carrier fluid 120. Carrier fluid may comprise hydrogel or other material that is immiscible with protease 115 and cells 120.

In FIG. 1, a first microfluidic channel and a second microfluidic channel can join at a junction such that the first fluid and the immiscible carrier fluid can intersect to reliably generate a plurality of droplets 124. In one embodiment, the droplets may comprise cells 102 and protease 115.

In another embodiment, the droplets may be configured to additionally and optionally include cell lysates, nucleic acids of cells, solid supports (e.g., beads), barcode oligonucleotides, or a combination thereof. The immiscible carrier fluid 120 may segment the first fluid to generate the plurality of droplets 124. For example, the plurality of droplets 124 can be generated immediately or substantially immediately after the junction of the first microfluidic channel and the second microfluidic channel. Droplets 124 may be generated immediately or substantially immediately after the intersection of the first fluid and the immiscible carrier fluid. The droplets may be generated without any sorting steps. In some instances, methods comprise incorporating a solid support, e.g., a bead (not shown) into the droplets. Controllably generating droplets containing a solid support therein can facilitate controlled combination of the solid support with one or more components downstream. Non-limiting examples of components downstream are cells, cell lysis reagents, cell lysates, nucleic acids, and reagents for nucleic acid synthesis, such as a nucleic acid amplification process.

Figure 2:
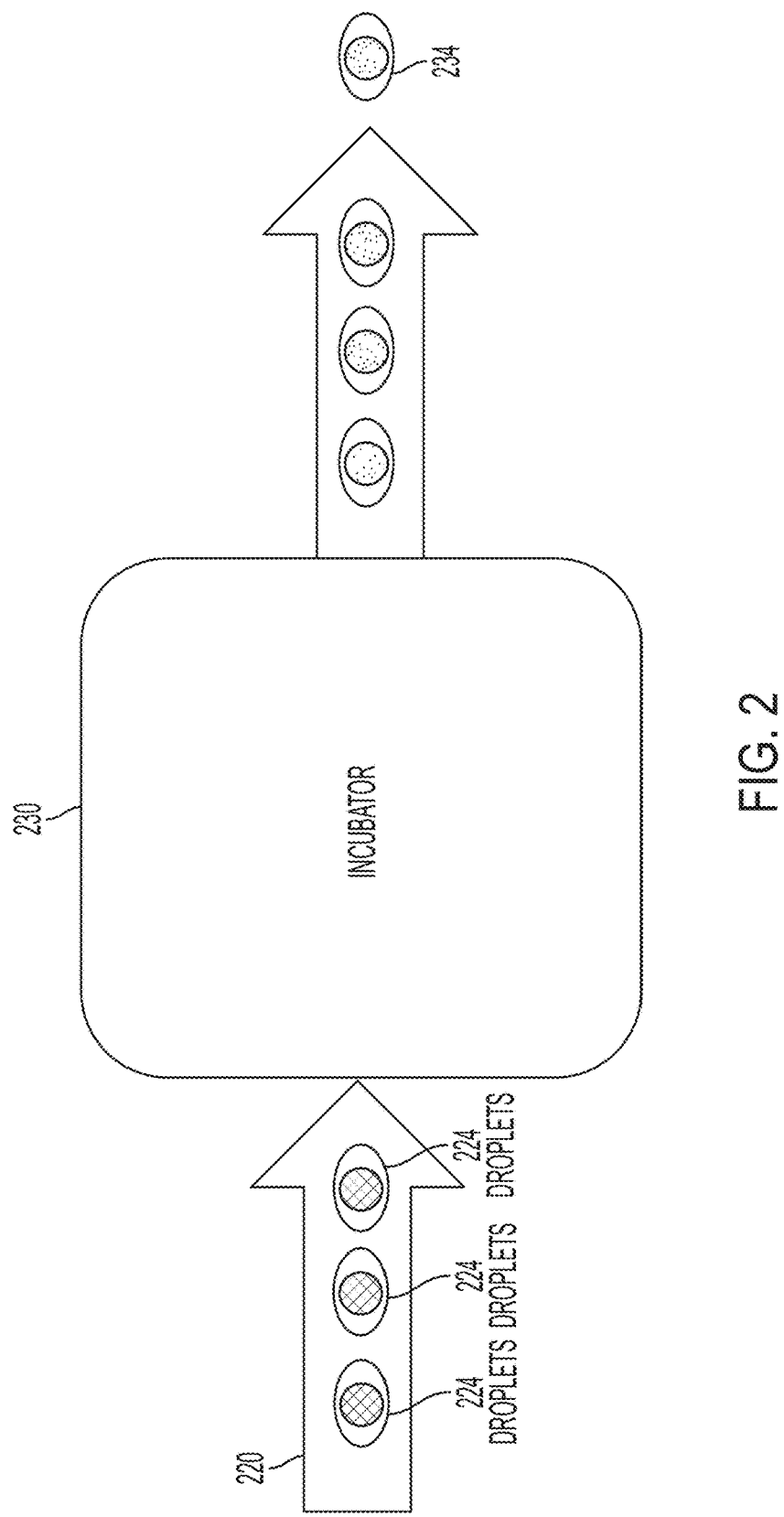
FIG. 2 schematically illustrates incubation of protease and cell droplets according to one embodiment of the disclosure.

FIG. 2 schematically illustrates incubation of protease and cell droplets according to one embodiment of the disclosure. In one embodiment, the process shown in FIG. 2 can be considered as the lysate preparation process. In FIG. 2, droplets 224 (cell and protease droplets 124, FIG. 1) are directed to incubator 230. Incubator 230 provides cell lysis and protease digestion. Droplets 224 are suspended in oil stream 220 as in FIG. 1. In certain embodiments, incubator 230 may incubate a one or more temperatures (e.g., 50° C. and 80° C.) for one or more intervals.

The output of incubator 230 is lysate droplets 234. Lysate droplets 234 may be used for genomic DNA amplification. Following the lysate preparation, the protease in the droplet is inactivated by heat denaturation and each droplet containing genome of an individual cells is paired with a molecular bar code and PCR amplification reagent.

Figure 3:
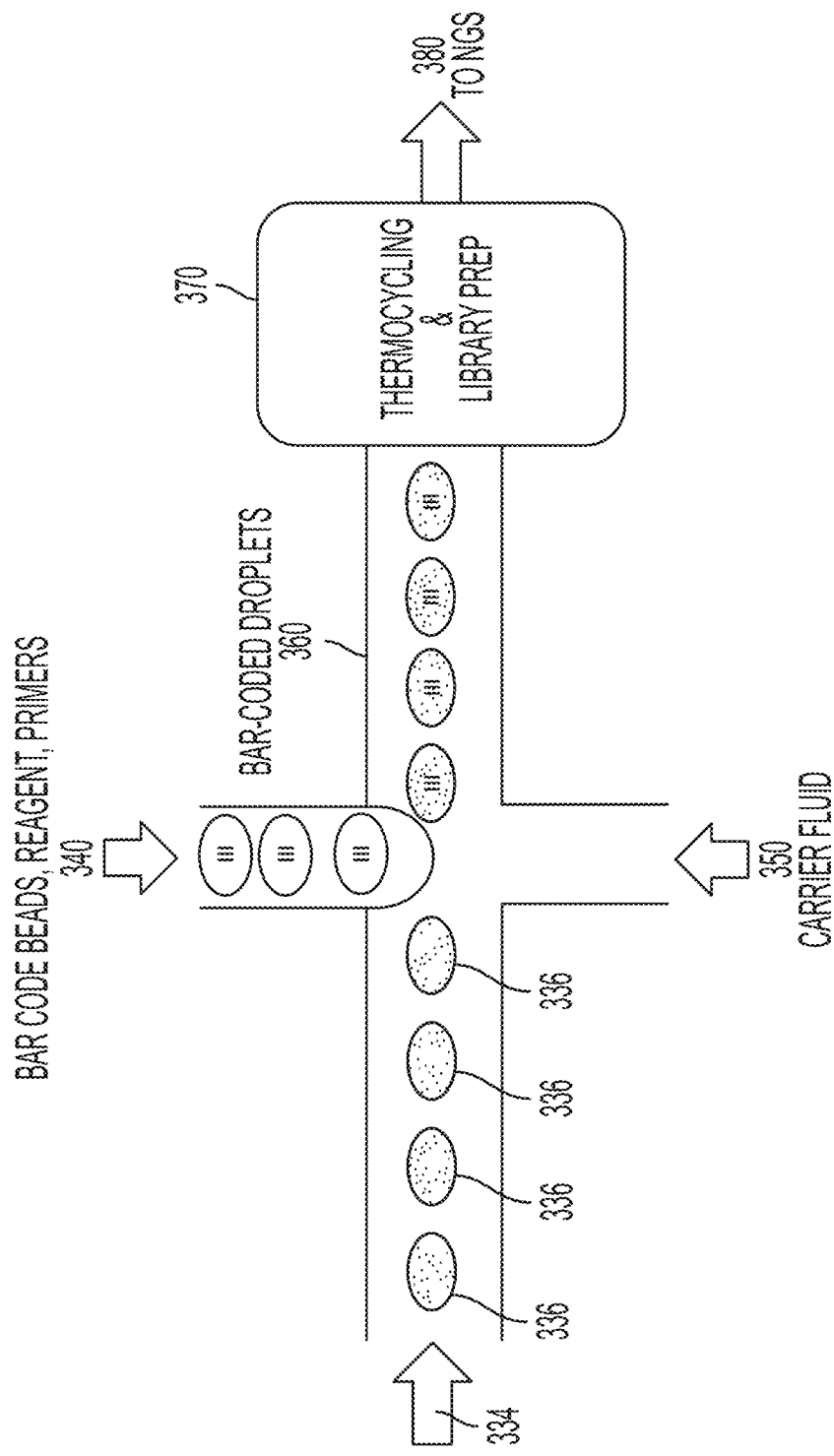
FIG. 3 schematically illustrates bar coding of an exemplary droplet according to one embodiment of the disclosure.

FIG. 3 schematically illustrates bar coding of an exemplary droplet according to one embodiment of the disclosure. In FIG. 3, stream 334 includes lysate droplets 336, substantially similar to the lysate droplet 234 of FIG. 2. In one embodiment, stream 340 may include bar code beads, reagent and primers. In one embodiment, carrier fluid 350 may be added. Second droplets 360 may comprise a cell identifier (e.g., barcode) and one or more primers specific to a plurality of regions of the genomic DNA. The primers may be designed and/or selected to target specific and desired regions of the genomic DNA.

In certain embodiments, barcoded droplets 340 may comprise bar-coded beads. As stated, one or more reagent may be introduced into the continuous stream 340. Stream 340 may comprise PCR primers and reagents designed for amplification. In one embodiment, specific regions of interest of the cell is amplified while tagging each amplicon with a unique cell barcode. This preserves the cell's identity and maturation profile.

In one embodiment, TaqMan™ PCR amplification reagent may be used. The resulting droplets 360 contain cell lysis, bar code and reagent mix. Droplets 360 are then thermo-cycled and library-prepped through instrument 370 to produce cell library 380. Cell library 380 may be subjected to NGS or further identification processing. The processes shown at FIGS. 1-3 provide a unique approach to profile SNVs and indel mutations at the single-cell level, deciphering the true cellular heterogeneity that defines a tumor sample.

The single-cell data enables direct assessment of clonal architecture with detection of mutation co-occurrence patterns. Rather than identifying variants that co-occur within a sub-clone from comparable bulk variant allele frequencies, single-cell resolution uncovers the true distribution of genotypes and their segregation pattern across subclones.

Figure 4:
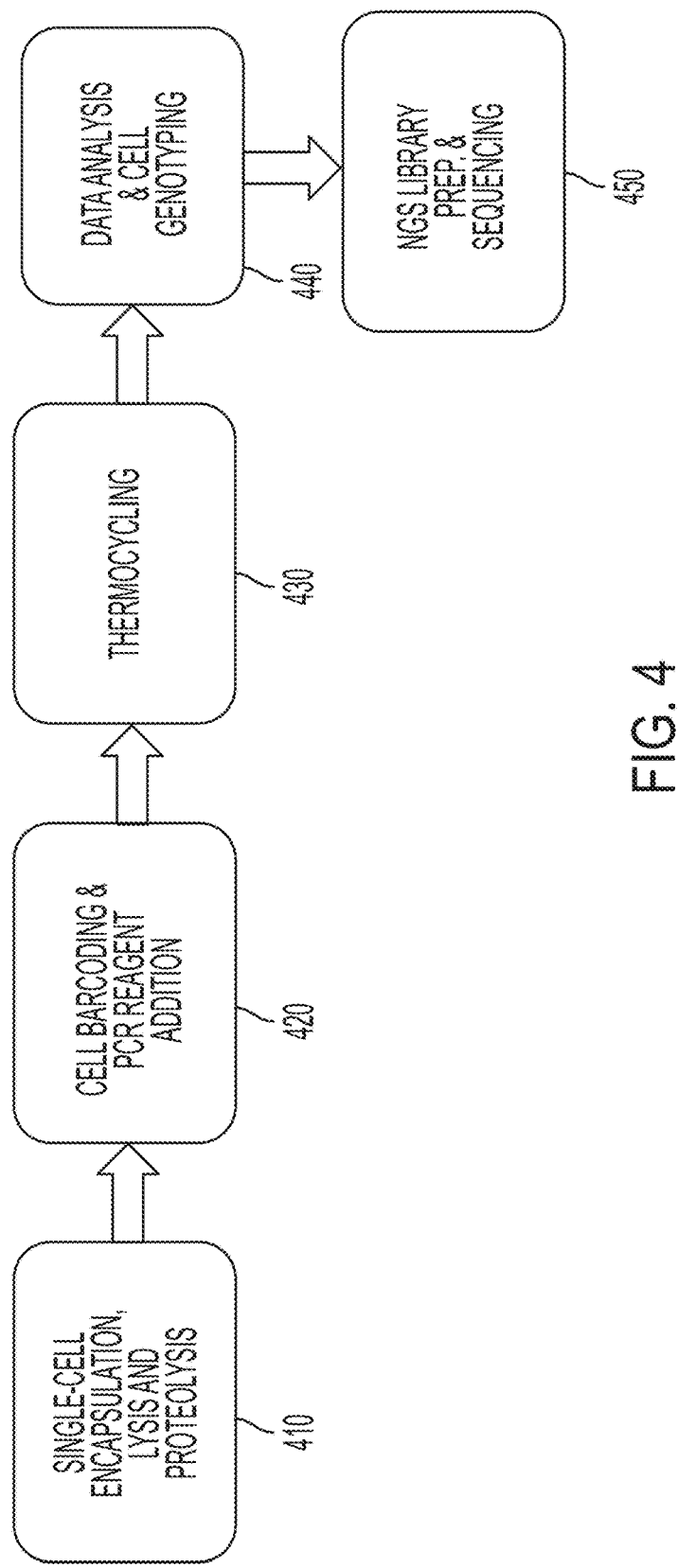
FIG. 4 illustrates an exemplary process for implementing the disclosed principles.

FIG. 4 illustrates an exemplary process for implementing the disclosed principles. The process of FIG. 4 starts ate step 410 with single-cells encapsulation, lysis and proteolysis. Step 410 may be implemented with one or more sub-steps as described in references to FIGS. 1 and 2. At step 420, the encapsulated single-cell is bar-coded. One or more PCR reagent may also be added to the bar-coded single-cell. At step 430, the droplet containing the bar-coded single-cell with reagent is thermocycled to amplify the genome of interest. At step 440, the amplified cells are analyzed and the cells are genotyped. At step 450, NGS library prep and sequencing is performed to identify variants in the cell samples.

As stated, in certain embodiments, the microfluidic workflow first encapsulates individual cells in droplets, lyses the cells and prepares the lysate for genomic DNA amplification using proteases. In certain embodiments, following the lysate preparation step, the proteases are inactivated via heat denaturation and droplets containing the genomes of individual cells are paired with molecular barcodes and PCR amplification reagents.

Example 1

Protease based droplet workflow for single-cell genomic DNA amplification and barcoding. In this example, the process flow discussed in FIG. 4 was implemented on a group of cells. To demonstrate advantages of the protease in the two-step workflow, in one embodiment, droplet-based single-cell TaqMan™ PCR reactions were performed targeting the SRY locus on the Y chromosome, present as a single copy in a karyotypically normal cell. PCR-Activated Cell Sorting ("PACS") were carried out on calcein violet stained DU145 prostate cancer cells encapsulated and lysed with or without the addition of a protease.

Figure 5B:
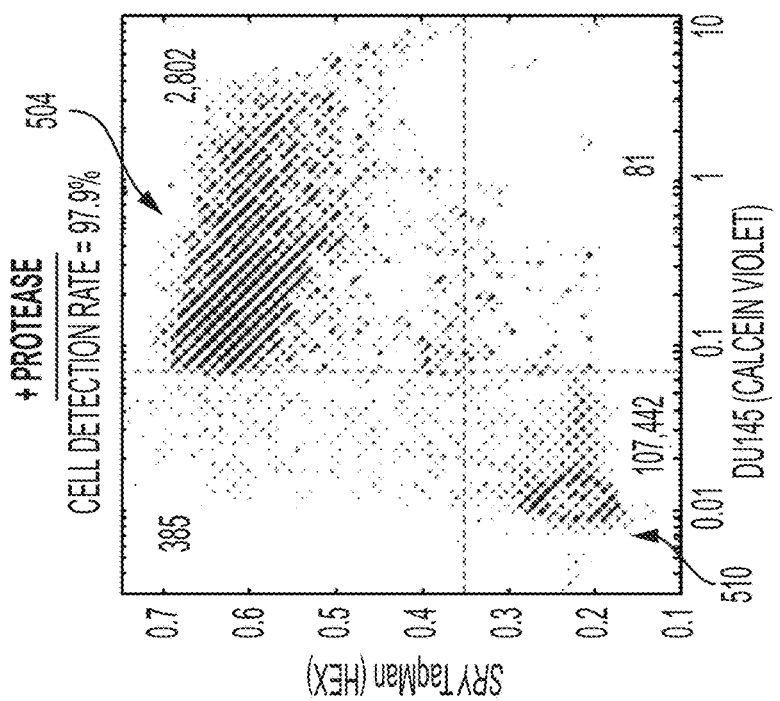
FIG. 5B shows the resulting cell distribution for an application of the disclosed embodiments for a sample with protease.
Figure 5A:
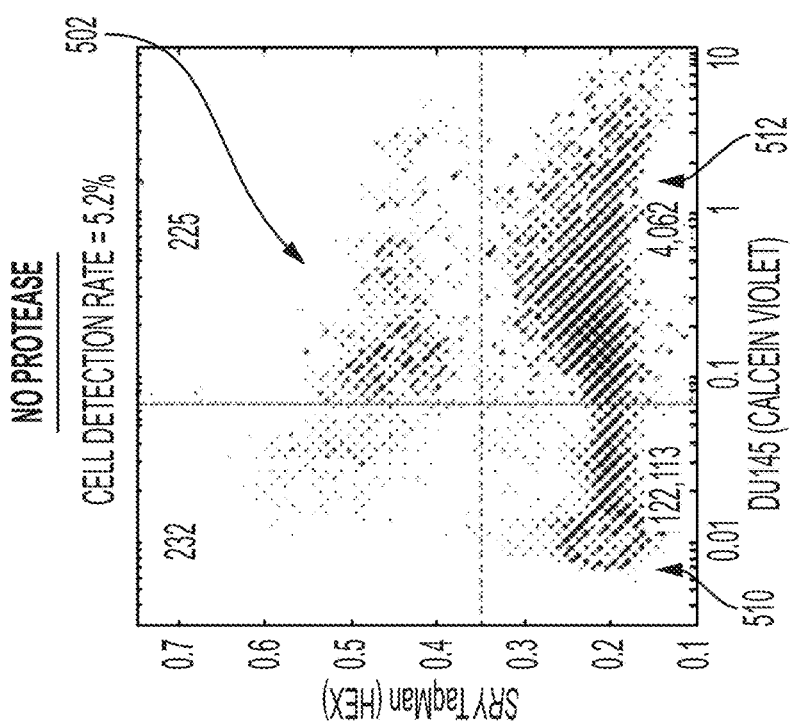
FIG. 5A shows cell distribution for an application of the disclosed embodiments without protease (no protease).

In the absence of protease during cell lysis, only 5.2% of detected DU145 cells were positive for TaqMan fluorescence. The inclusion of the protease resulted in a dramatically improved SRY locus detection rate of 97.9%. The results is shown in FIGS. 5A and 5B. In FIG. 5A, no protease was used and the denaturation rate was 5.2%. In FIG. 5B, protease was used and the denaturation rate of 97.9% was obtained.

More specifically, FIGS. 5A and 5B show the resulting cell distribution for an application of the disclosed embodiments for a sample with no-protease and a sample with protease. Here, cells (pseudo colored in blue (numbered 510 in FIGS. 5A and 5B)) were encapsulated with lysis buffer containing protease (yellow (numbered 512 in FIG. 5A)) and incubated to promote proteolysis. Protease activity was then thermally inactivated and the droplets containing the cell lysate are paired and merged with droplets containing PCR reagents and molecular barcode-carrying hydrogel beads (pseudo colored in purple).

Next, the determination was made as to whether the two-step workflow was also required for single-cell barcoding of amplicons targeting 8 genomic loci located in TP53, DNMT3A, IDH1, IDH2, FLT3 and NPM1. To this end, hydrogel beads were synthesized with oligonucleotides containing both cell identifying barcodes and different gene specific primer sequences. These barcoded beads were microfluidically combined with droplets containing cell lysate generated with or without the protease reagent according to the disclosed process of FIG. 4.

Prior to PCR amplification, the oligonucleotides are photo-released from the hydrogel supports with UV exposure. Consistent with our earlier single-cell TaqMan™ reaction observations, amplification of the targeted genomic loci was substantially improved by use of a protease during cell lysis. Although similar numbers of input cells were used for both conditions, the use of protease enabled greater sequencing library DNA yields as assessed by a Bioanalyzer.

Figure 5D:
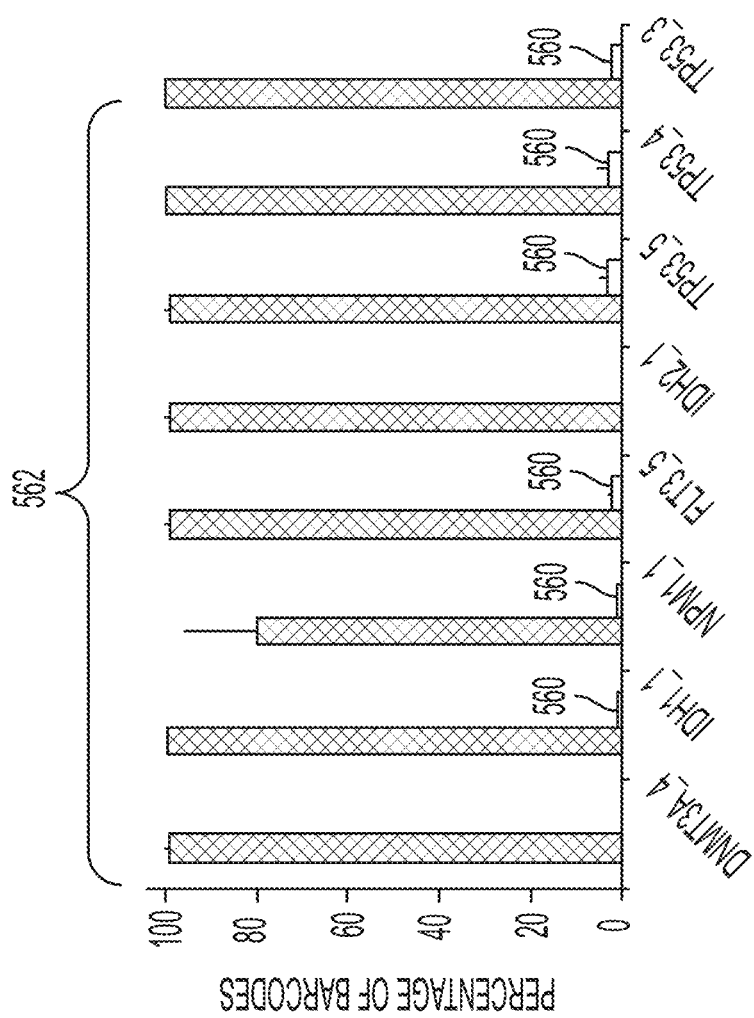
FIG. 5D shows the percentage of barcode reads for the eight targeted genomic loci for a sample with protease and a sample without protease.

The results is shown in FIGS. 5C and 5D. Specifically, FIG. 5C shows the NGC library yields and size distribution at 371 base pairs. FIG. 5C shows that when protease enzyme was left out of the workflow for single-cell gDNA PCR in droplets, only ~5% of DU145 cells (viability stained on the x-axis) were positive for SRY TaqMan reaction fluorescence (y-axis). Using protease during cell lysis 552 improves the DU145 cell detection rate to ~98% (points in upper right quadrant 550). Points in the plot represent droplets.

FIG. 5D shows the percentage of barcode reads for the eight targeted genomic loci. The results of FIG. 5D show bioanalyzer traces of sequencing libraries prepared from cells processed through the workflow with (black trace 562) or without (red trace 560) the use of protease indicates that PCR amplification in droplets is improved with proteolysis. The two-step workflow with protease enables better sequencing coverage depth per cell across the 8 amplified target loci listed on the x-axis.

Moreover, following sequencing, the average read coverage depth for the 8 targets from each cell was considerably higher when protease was used in the workflow. This data demonstrates the advantage of the two-step workflow for efficient amplification across different genomic loci for targeted single-cell genomic sequencing with molecular barcodes.

Example 2

Analysis of AML clonal architecture. Samples were obtained from a patient with AML at the times of diagnosis, remission and relapse. Having developed the core capability to perform targeted single-cell DNA sequencing, we next sought to apply the technology to the study of clonal heterogeneity in the context of normal karyotype AML.

To provide variant allele information at clinically meaningful loci, we developed a 62 amplicon targeted panel that covers many of the 23 most commonly mutated genes associated with AML progression. The result is tabulated at Table 1 of FIG. 6. Following optimization for uniformity of amplification across the targeted loci (see Table 1), the panel was then used for single-cell targeted sequencing on AML patient bone marrow aspirates collected longitudinally at diagnosis, complete remission and relapse. Following thawing of frozen aspirates, the cells were quantified and immortalized Raji cells were added to the sample to achieve an approximate 1% spike in cell population. Known heterozygous SNVs within the Raji cells served as a positive control for cell type identification and a way to assess allele dropout in the workflow. Cell suspensions were then emulsified and barcoded with our workflow prior to bulk preparation of the final sequencing libraries. Total workflow time for each sample was less than two days. MiSeg™ runs generating 250 bp paired-end reads were performed for each of the three samples that were barcoded.

On average, 74.7% of the reads (MAPQ>30) were associated with a cell barcode and correctly mapped to one of the 62-targeted loci as shown in FIG. 7A. Specifically, FIG. 7A is a table displaying key metrics from the diagnosis, remission and relapse single cell DNA sequencing run from an AML patient.

Figure 7B:
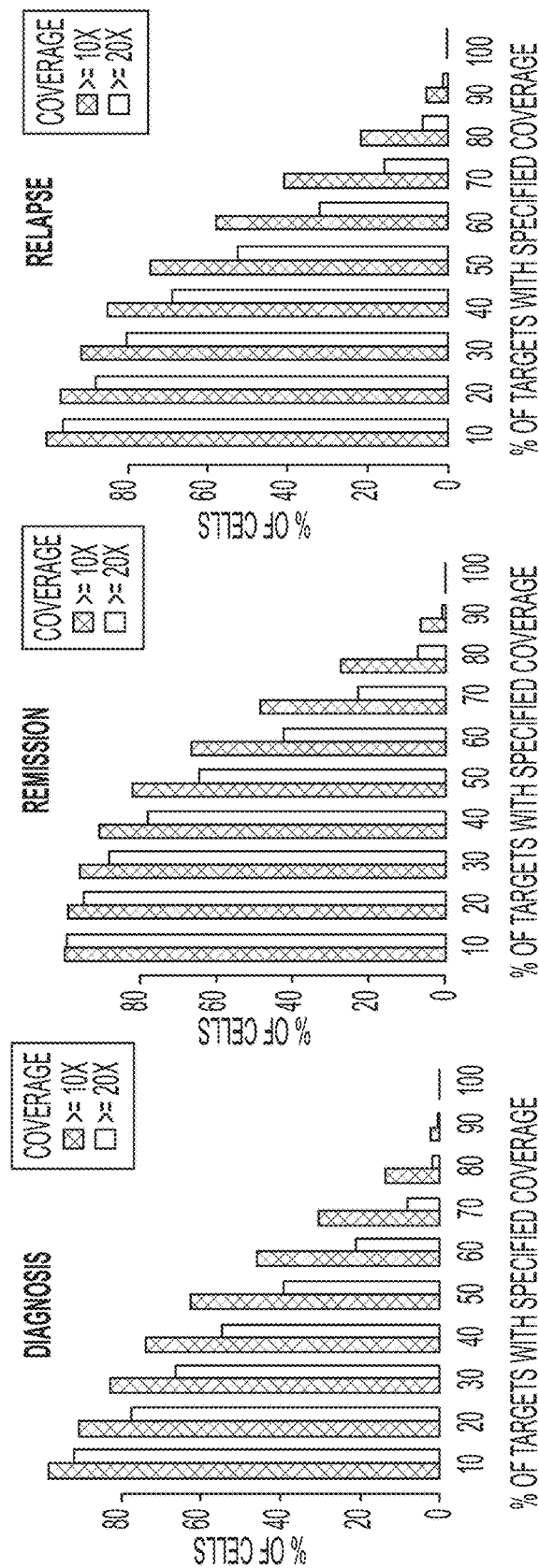
FIG. 7B shows the performance of the panel across the targeted loci for each of the three testing stages.

Performance of the panel across the targeted loci is shown in FIG. 7B for each of the three stages of testing.

The Raji cell spike in detection rate across the three sample runs averaged 2.4% and the average allele dropout rate, calculated from two separate heterozygous TP53 SNVs present in the Raji cells, was 5.5% (see FIG. 7).

The allele dropout rate in FIG. 7 represents the percentage of cells within a run, averaged across the two loci, where the known heterozygous SNV was incorrectly genotyped as either homozygous wild type or homozygous mutant.

Figure 8:
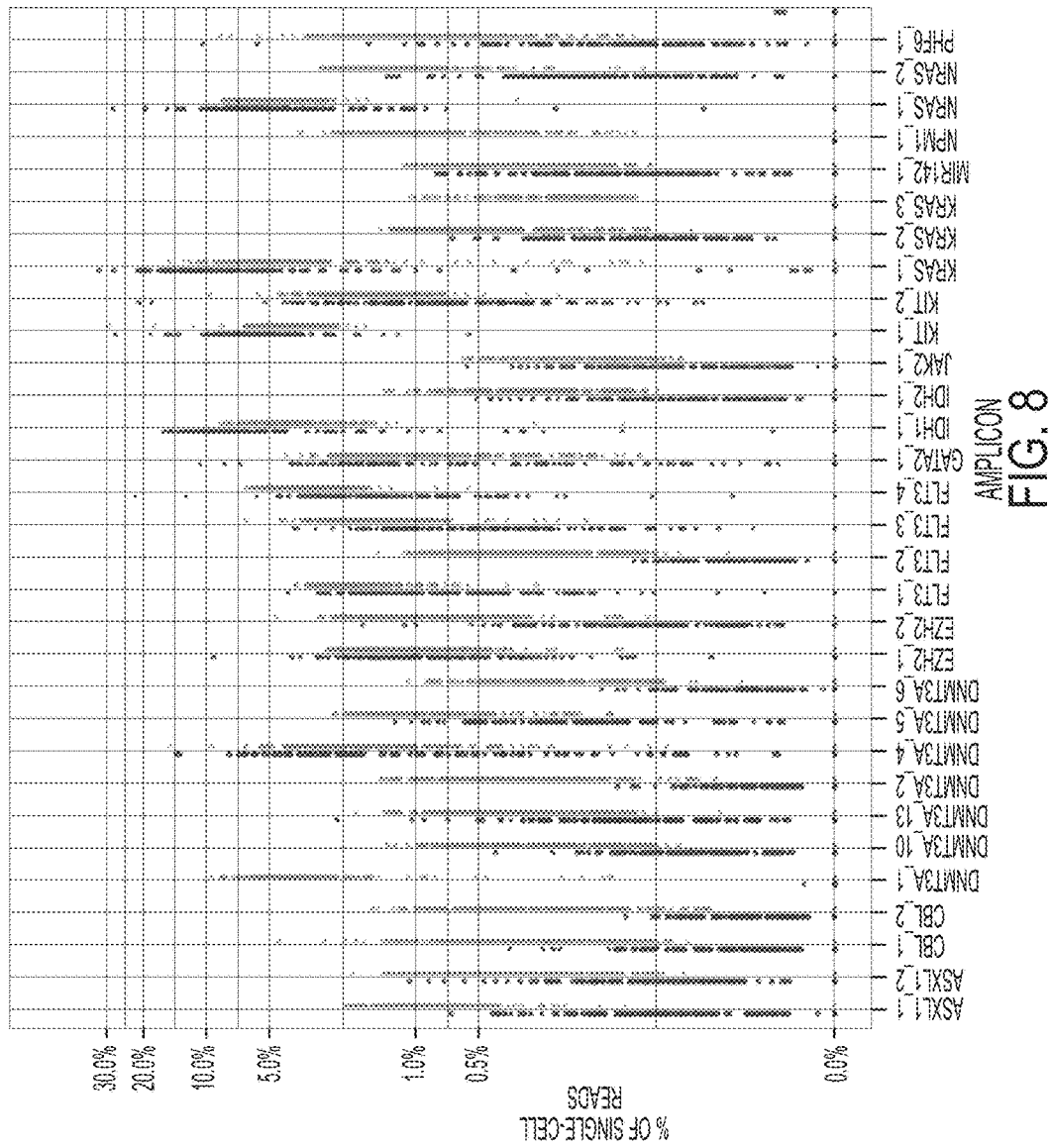
FIG. 8 shows the performance of the AML panel across the targeted locis of AML genome tested according to the disclosed embodiments.
Figure 8:
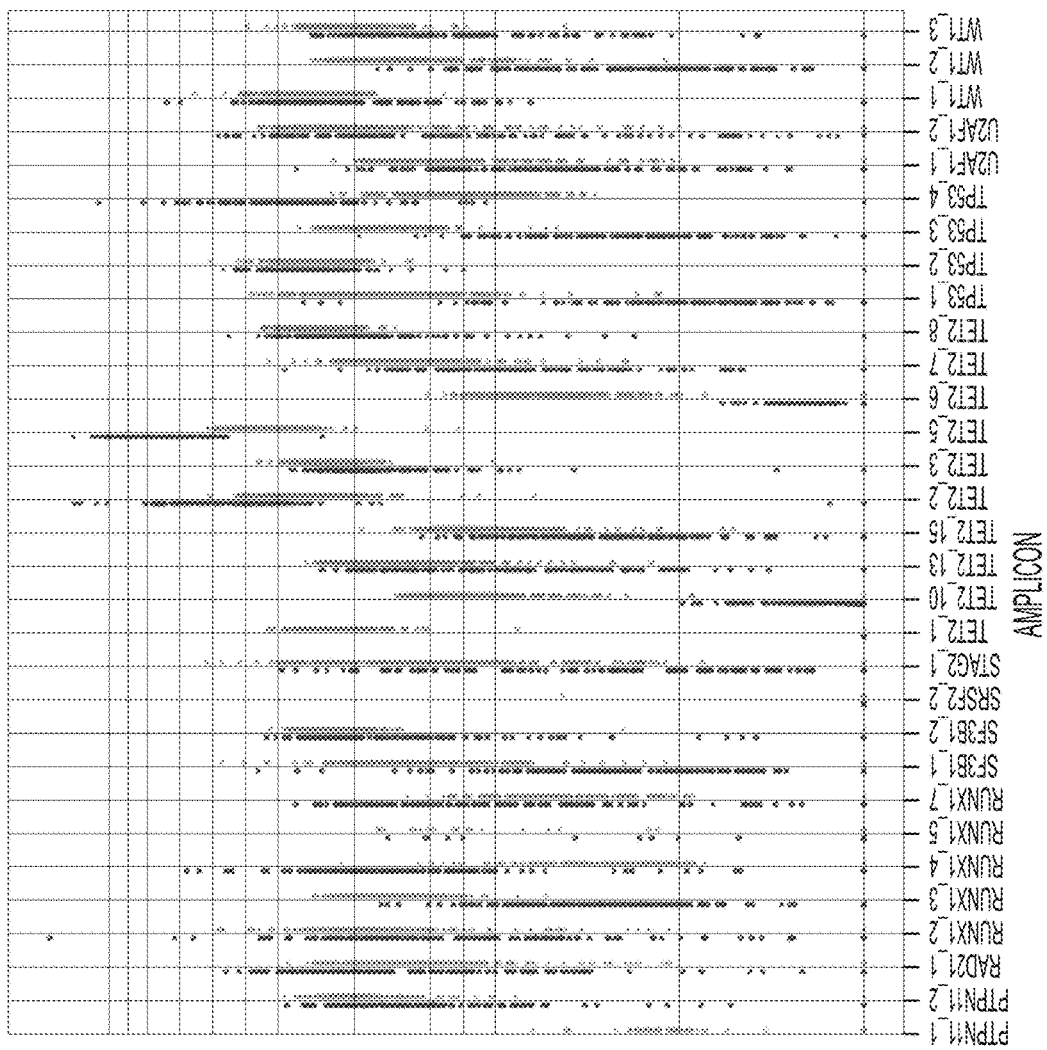

Performance of the AML panel across the targeted loci is shown in FIG. 8.

Figure 10:
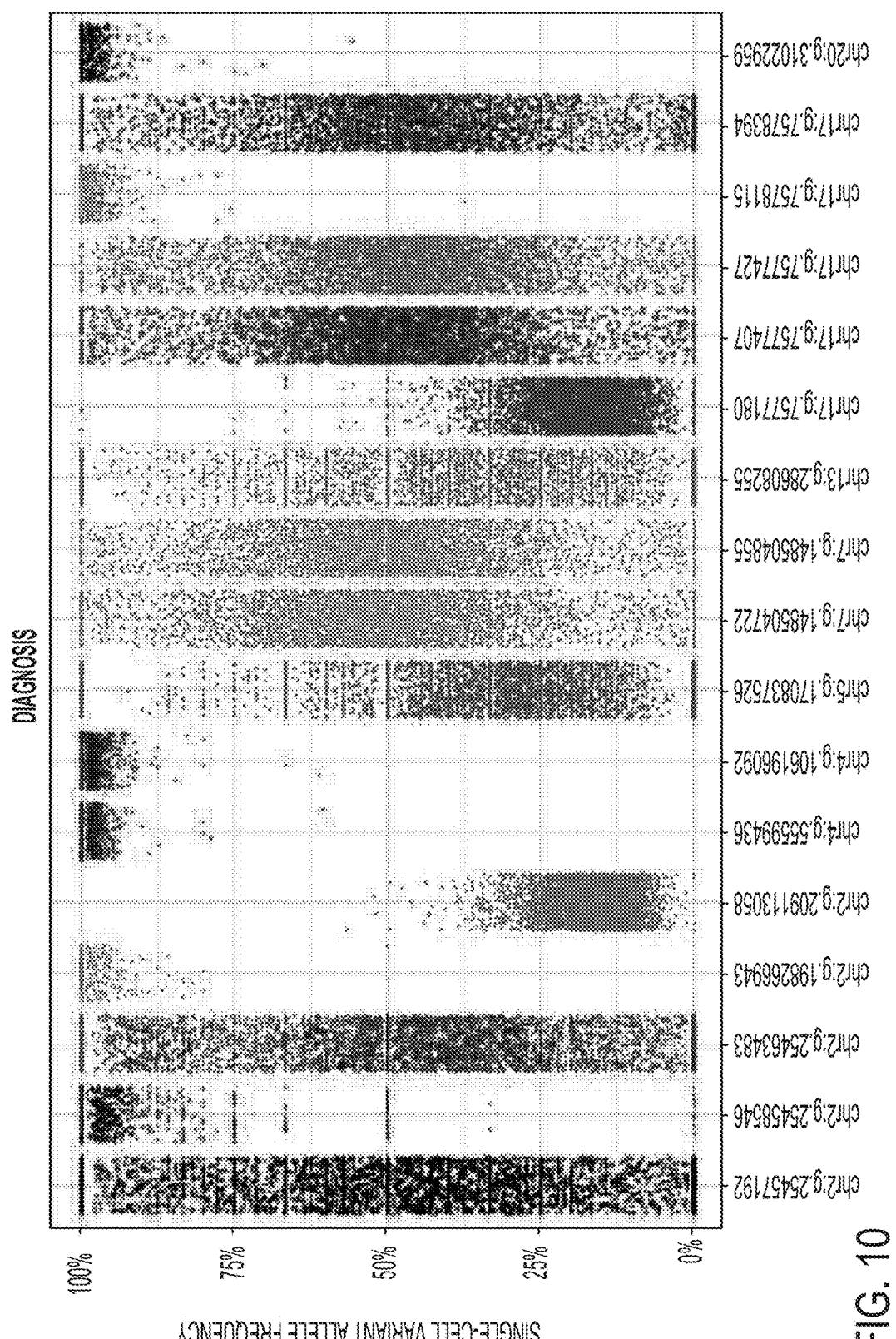
FIG. 10 shows the presence of each of the 17 alleles of FIG. 9 in different sample populations (diagnosis, remission and relapse).
Figure 10:
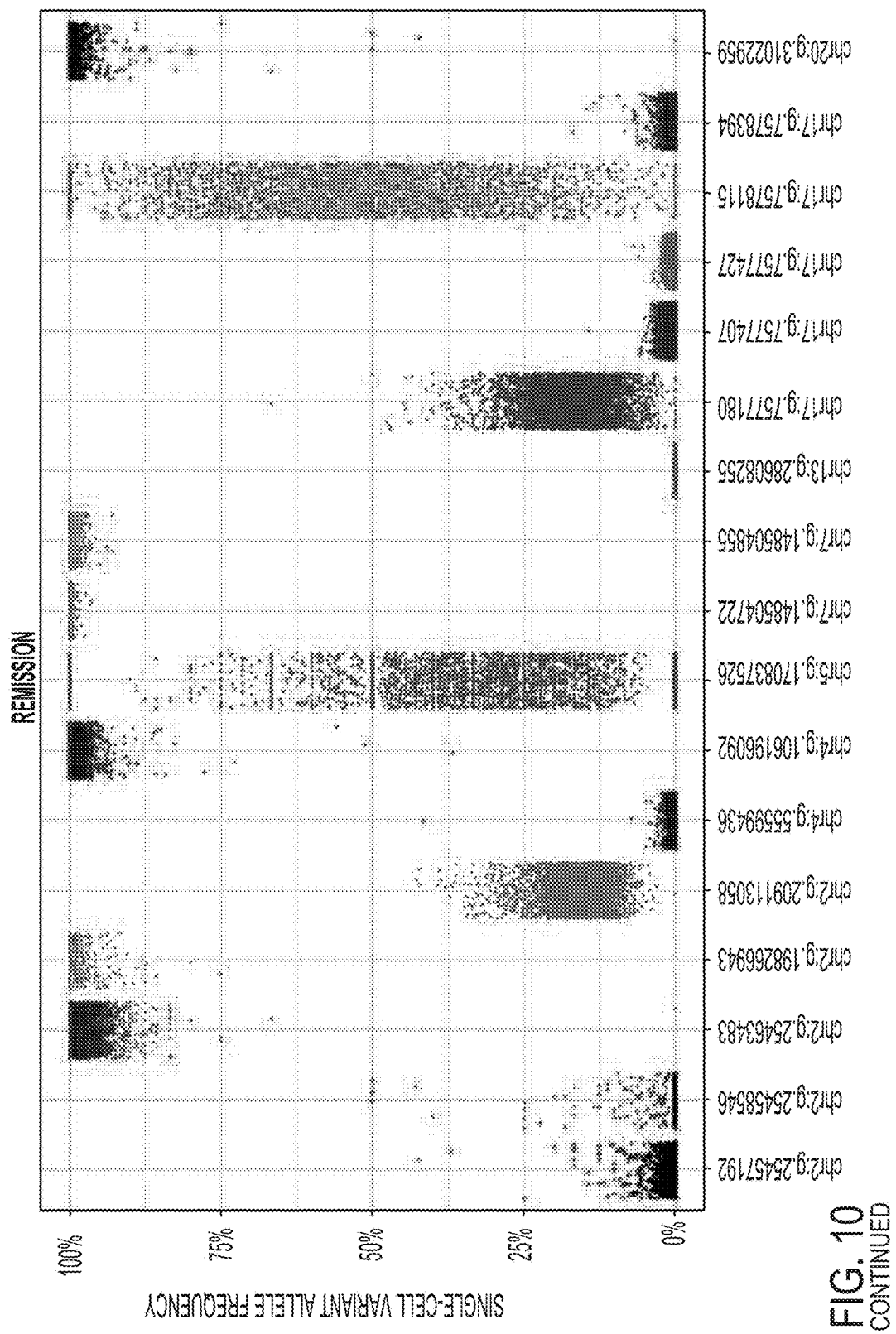
Figure 10:
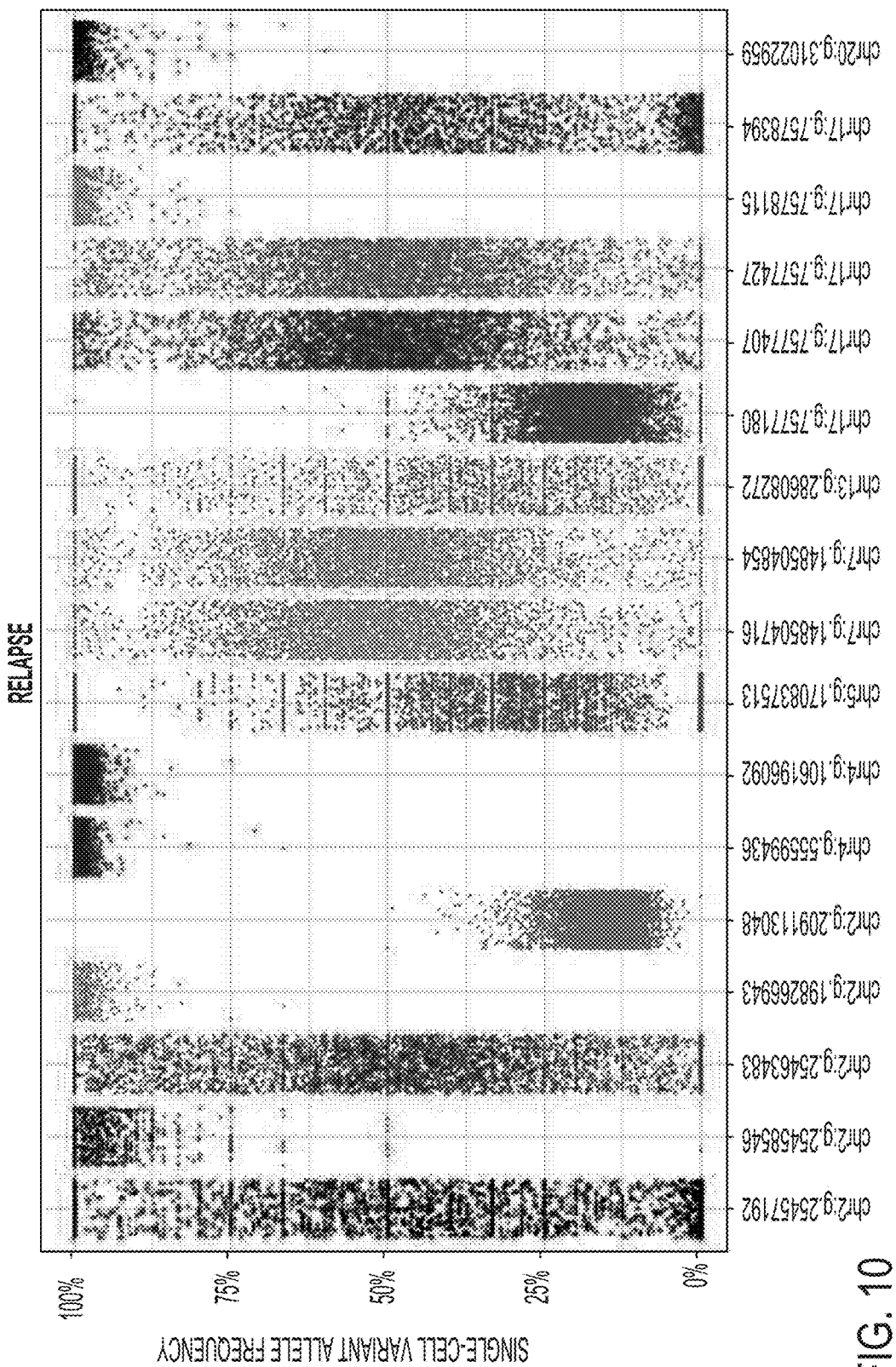

Using conventional genotype calling algorithms, a total of 17 variant alleles for this patient were identified. The identified alleles are shown at FIG. 9. FIG. 10 shows the presence of each of the 17 alleles of FIG. 9 in different sample populations (diagnosis, remission and relapse).

While 13 of these variants occurred in noncoding DNA, three non-synonymous SNVs were found in coding regions of TP53 (H47R), DNMT3A (R899C) and ASXL1 (L815P) from all three longitudinal samples. This is shown in FIGS. 11A, 11B and 11C.

Figures 11A, 11B:
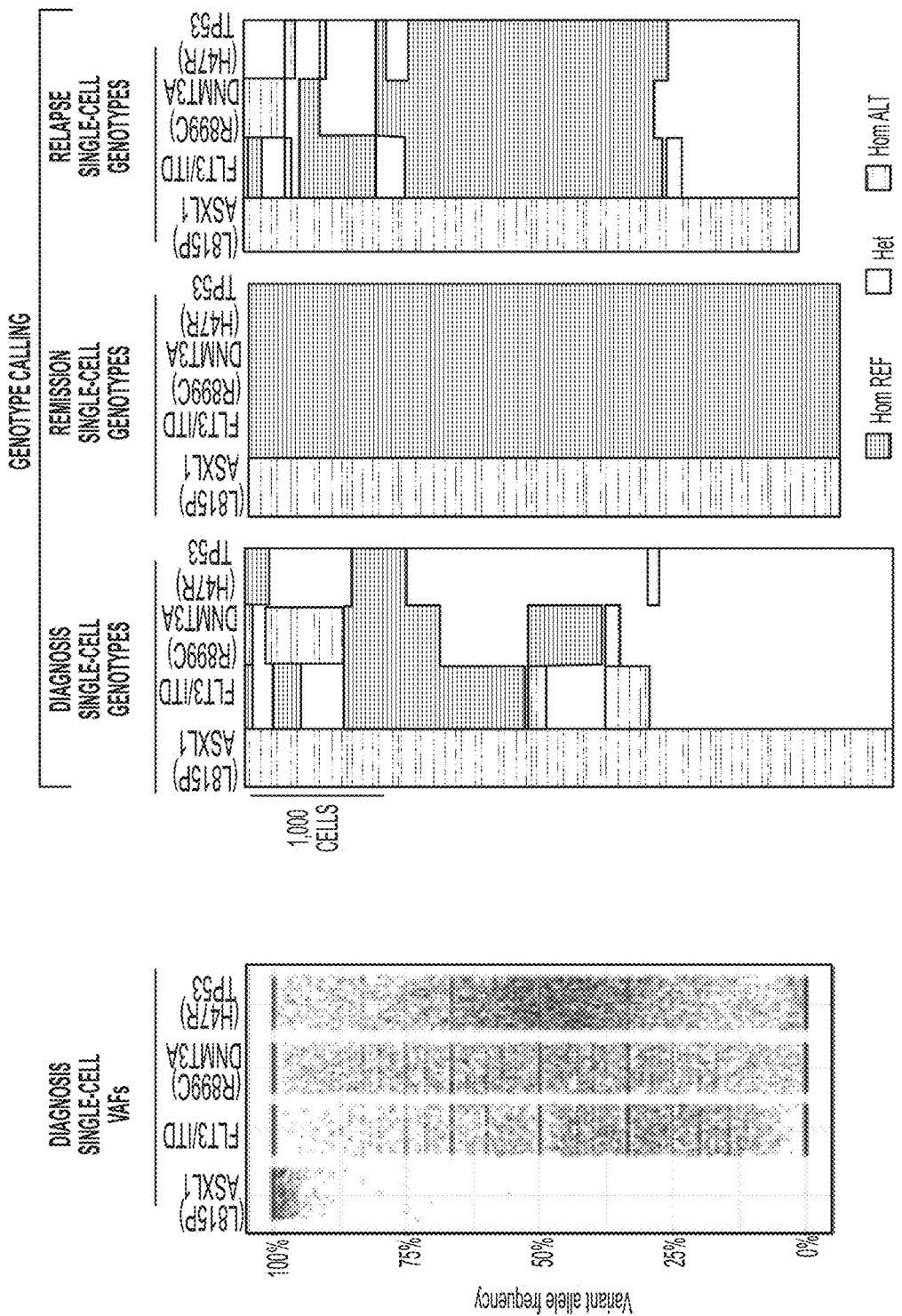
FIG. 11A shows diagnosis sample single-cell VAFs for each of the 4 non-synonymous mutations identified for the AML patient.
FIG. 11B shows the heat maps denoting single-cell genotypes for the three longitudinal AML patient samples. Non-patient Raji cells have been removed.

FIG. 11A shows diagnosis sample single-cell VAFs for each of the 4 non-synonymous mutations identified for the AML patient. Here, the variant frequency of each allele is shown according to the shading.

FIG. 11B shows the heat maps denoting single-cell genotypes for the three longitudinal AML patient samples. The presence of a heterozygous alternate (ALT) allele is shown in red. Homozygous alternate alleles are shown in dark red and reference alleles are depicted in grey.

Figure 11C:
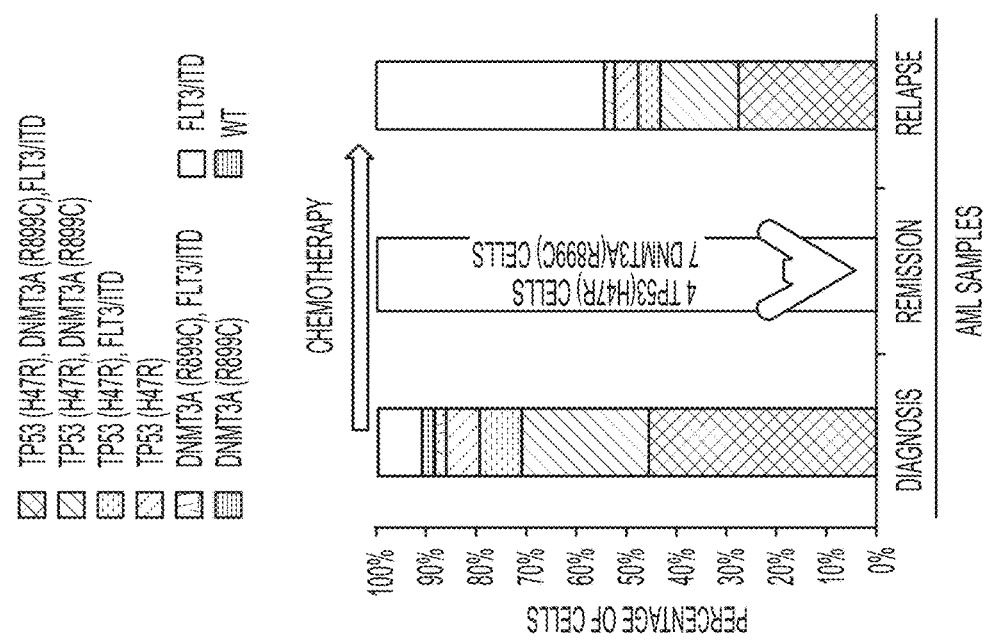
FIG. 11C shows the clonal populations identified from clinical bone marrow biopsies taken at the time of diagnosis, remission and relapse. Non-patient Raji cells have been removed.

FIG. 11C shows the clonal populations identified from clinical bone marrow biopsies taken at the time of diagnosis, remission and relapse. Wild Type indicates cell that had reference genome sequence for TP53, DNMAT3A and FLT3, but were homozygous for the ASXL1 (L815P) mutation.

ASXL1 (L815P) is a previously reported common polymorphism (dbSNP: rs6058694) and was likely present in the germline since it was found in all cells throughout the course of the disease. Additionally, a 21 bp internal tandem duplication (ITD) in FLT3 was detected in cells from the diagnosis and relapse samples. FLT3/ITD alleles are found in roughly a quarter of newly diagnosed adult AML patients and are associated with poor prognosis. A total of 13,368 cells (4,456 cells per run average) were successfully genotyped at the four variant genomic loci (See FIGS. 7, 11A and 11B).

A comparison of the clonal populations from the diagnosis, remission and relapse samples indicates that the patient initially achieved complete remission, although having 10 mutant cells demonstrates the presence of minimal residual disease ("MRD") at this time point (See FIG. 11C).

Despite the initial positive response to therapy, the reemergence of the clones present at diagnosis in the relapse sample indicates that it was ineffective at eradicating all of the cancer cells and, in this instance, did not dramatically remodel the initial clonal architecture of the tumor. Single-cell sequencing of additional cells from the remission sample may be required to test this hypothesis and identify additional MRD clones.

Figure 12:
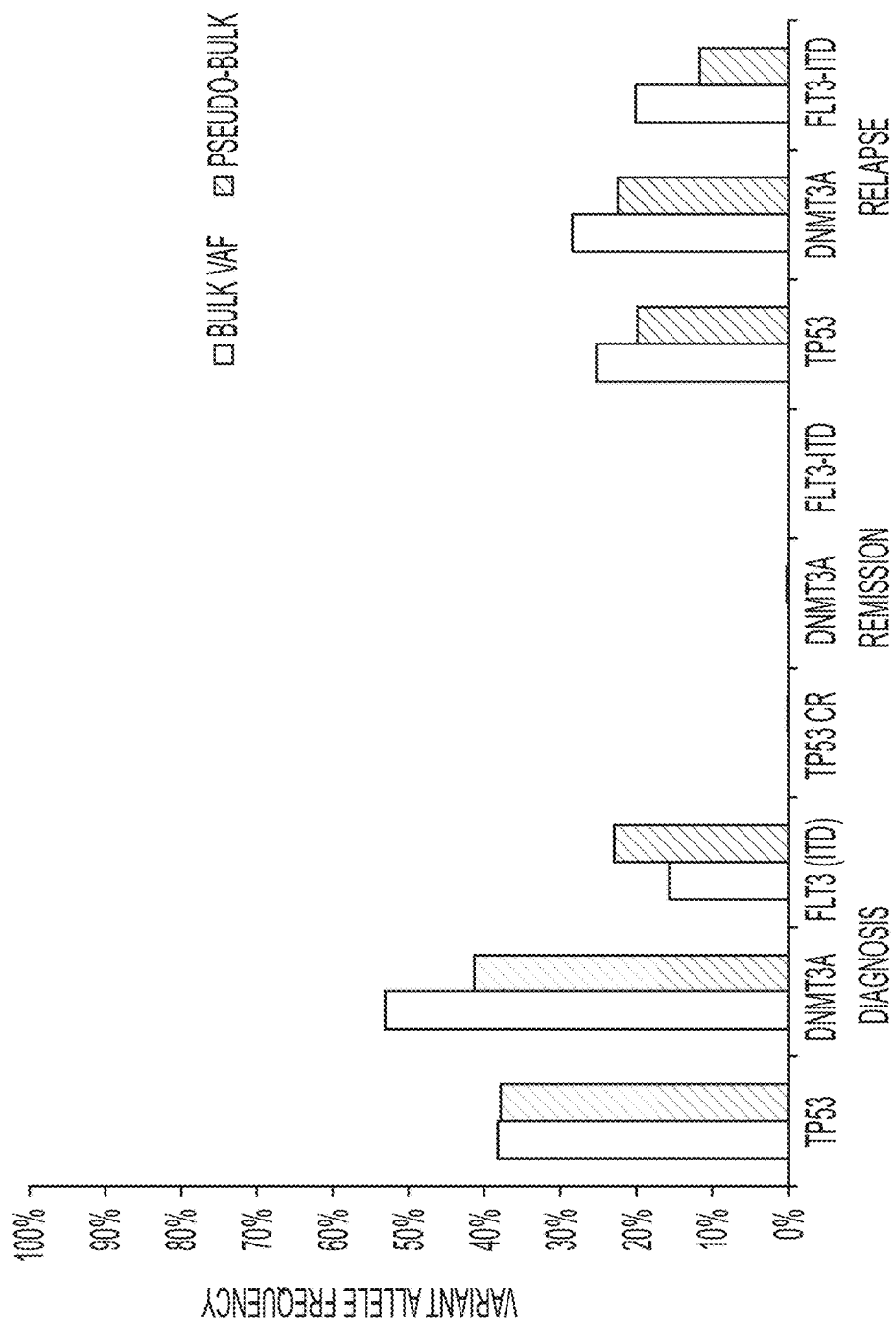
FIG. 12 shows the comparative results for bulk VAFs versus VAFs acquired from the disclosed single-cell sequencing workflow when the barcode identifiers were removed.

To assess the performance of the disclosed single-cell approach relative to conventional next generation sequencing (e.g., online methods, discussed below), bulk variant allele frequencies (VAFs) were obtained for the relevant mutations in two of the biopsy samples. The bulk VAFs were comparable to the VAFs acquired from the disclosed single-cell sequencing workflow (pseudo bulk VAFs) when the barcode identifiers are removed and the reads are analyzed in aggregate. The results are shown at FIG. 12.

Figure 13:
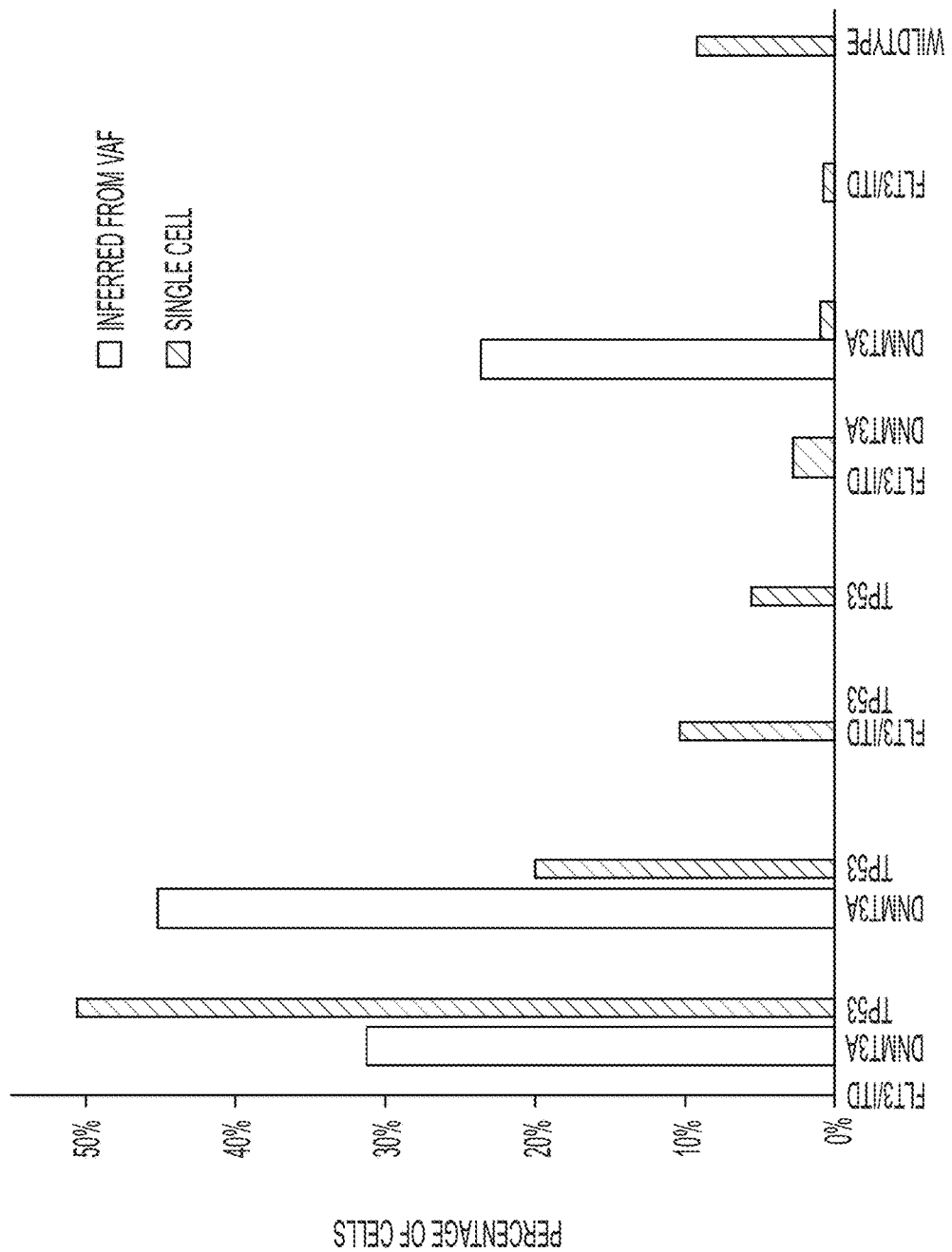
FIG. 13 shows a comparison of single-cell sequencing data from the diagnosis sample obtained from our workflow and a simple clonal inference of the diagnosis cell clonal populations produced from the bulk VAFs. Non-patient Raji cells have been removed.

We next used the bulk sample VAFs to infer clonal architecture and compare it to the clonal populations obtained with our single-cell sequencing approach. The simplest model of inferred clonality predicts a significant DNMT3A (R899C) single mutant population indicative of founder mutation status (FIG. 13). FIG. 13 shows cells with greater than 20× read coverage of amplicon. This shows that disclosed workflow with protease enables better sequencing coverage depth per cell across the 8 amplified target loci listed on the x-axis.

Interestingly, the single-cell sequencing data does not support this model as only a relatively small DNMT3A single mutant population is observed and this population is at a frequency that can be explained by allele dropout. In contrast, our results suggest that the SNV in TP53 could be the founding mutation since the size of the TP53 (H47R) single mutant clone is larger than what would be expected from allele dropout. Our single-cell approach also unambiguously identified the TP53, DNMT3A and FLT3/ITD triple mutant population as the most abundant neoplastic cell type in the diagnosis and relapse samples (See 11C). Moreover, the identification of this clone strongly supports a model where the mutations were serially acquired during the progression of the disease.

As shown in Example 2, the disclosed embodiments provide rapid and cost-effective targeted genomic sequencing of thousands of AML cells in parallel which has not been feasible with conventional technologies. Applying the disclosed methods, system and apparatus to the study of larger AML patient populations will likely lead to correlations between clonal heterogeneity and clinical outcomes. Although the exemplary embodiments were focused on AML in this study, the disclosed principles are applicable to other cancer cell types and profiling of solid tumors that may have been dissociated into single-cell suspensions. This capability is poised to complement an increased scientific appreciation of the role that genetic heterogeneity plays in the progression of many cancers as well as a desire by clinicians to make personalized medicine a widespread reality.

The following provides additional information regarding certain implementation of the disclosed embodiments.

Online Methods—Cell and Patient Samples—

Raji B-lymphocyte cells were cultured in complete media (RPMI 1640 with 10% fetal bovine serum (FBS), 100 U/ml penicillin, and 100 µg/ml streptomycin) at 37° C. with 5% $CO_2$. Cells were pelleted at 400 g for 4 min and washed once with HBSS and resuspended in PBS that was density matched with OptiPrep (Sigma-Aldrich) prior to encapsulation in microfluidic droplets.

The clinical AML samples were obtained from a 66 year old man diagnosed with AML, French-American-British (FAB) classification M5. Pre-treatment diagnostic bone marrow biopsy showed 80% myeloblast and cytogenetic analysis showed normal male karyotype. The patient received an induction chemotherapy consisted of fludarabine, cytarabine and idarubicin. Day 28 bone marrow aspiration showed morphological complete remission (CR). The patient received additional 2 cycles of consolidation therapy with the same combination but approximately 3 months after achieving CR, his AML relapsed with 48% blast. The patient was subsequently treated with azacitidine and sorafenib chemotherapy and achieved second CR. The patient then underwent allogeneic stem cell transplant from his matched sibling but approximately 2 months after transplant, the disease relapsed. The patient was subsequently treated with multiple salvage therapies but passed away from leukemia progression approximately 2 years from his original diagnosis. Bone marrow from original diagnosis, first CR, and first relapse were analyzed. Patient samples were collected under an IRB approved protocol and patients singed the consent for sample collection and analysis. The protocol adhered to the Declaration of Helsinki.

Frozen bone marrow aspirates were thawed at the time of cell encapsulation and resuspended in 5 ml of FBS on ice, followed by a single wash with PBS. All cell samples were quantified prior to encapsulation by combining 5 µl aliquots of cell suspension with an equal amount of trypan blue (ThermoFisher), then loaded on chamber slides and counted with the Countess Automated Cell Counter (ThermoFisher). The Raji cells were added to the bone marrow cell samples to achieve a ~1% final spike-in concentration.

Fabrication and Operation of Microfluidic Device—

A microfluidic device was constructed consistent with the disclosed principles. The microfluidic droplet handling on devices were made from polydimethylsiloxane (PDMS) molds bonded to glass slides; the device channels were treated with Aquapel to make them hydrophobic. The PDMS molds were formed from silicon wafer masters with photolithographically patterned SU-8 (Microchem) on them. The devices operated primarily with syringe pumps (NewEra), which drove cell suspensions, reagents and fluorinated oils (Novec 7500 and FC-40) with 2-5% PEG-PFPE block-copolymer surfactant into the devices through polyethylene tubing. Merger of the cell lysate containing droplets with the PCR reagent/barcode bead droplets was performed using a microfluidic electrode.

Generation of Barcode Containing Beads—

Barcoded hydrogel beads were made as previously reported in Klein et al. Briefly, a monomeric acrylamide solution and an acrydite-modified oligonucleotide were emulsified on a dropmaker with oil containing TEMED The TEMED initiates polymerization of the acrylamide resulting in highly uniform beads. The incorporated oligonucleotide was then used as a base on which different split-and-pool generated combinations of barcodes were sequentially added with isothermal extension. Targeted gene-specific primers were phosphorylated and ligated to the 5' end of the hydrogel attached oligonucleotides. ExoI was used to digest non-ligated barcode oligonucleotides that could otherwise interfere with the PCR reactions. Because the acrydite oligo also has a photocleavable linker (required for droplet PCR), barcoded oligonucleotide generation could be measured. We were able to convert approximately 45% of the base acrydite oligonucleotide into full-length barcode with gene specific primers attached. Single bead sequencing of beads from individual bead lots was also performed to verify quality of this reagent.

Cell Encapsulation and Droplet PCR—Following density matching, cell suspensions were loaded into 1 ml syringes and co-flowed with an equal volume of lysis buffer (100 mM Tris pH 8.0, 0.5% IGEPAL, proteinase K 1.0 mg/ml) to prevent premature lysing of cells3. The resultant emulsions were then incubated at 37° C. for 16-20 hours prior to heat inactivation of the protease.

Droplet PCR reactions consisted of 1× Platinum Multiplex PCR Master Mix (ThermoFisher), supplemented with 0.2 mg/ml RNAse A. Prior to thermocycling, the PCR emulsions containing the barcode carrying hydrogel beads were exposed to UV light for 8 min to release the oligonucleotides. Droplet PCR reactions were thermocycled with the following conditions: 95° C. for 10 min, 25 cycles of 95° C. for 30 s, 72° C. for 10 s, 60° C. for 4 min, 72° C. for 30 s and a final step of 72° C. for 2 min. Single-cell TaqMan reactions targeting the SRY locus were performed as previously described.

DNA Recovery and Sequencing Library Preparation—

Following thermocycling, emulsions were broken using perfluoro-1-octanol and the aqueous fraction was diluted in water. The aqueous fraction was then collected and centrifuged prior to DNA purification using 0.63× of SPRI beads (Beckman Coulter). Sample indexes and Illumina adaptor sequences were then added via a 10 cycle PCR reaction with 1× Phusion High-Fidelity PCR Master Mix. A second 0.63× SPRI purification was then performed on the completed PCR reactions and samples were eluted in 10 µl of water. Libraries were analyzed on a DNA 1000 assay chip with a Bioanalyzer (Agilent Technologies), and sequenced on an Illumina MiSeq with either 150 bp or 250 bp paired end multiplexed runs. A single sequencing run was performed for each barcoded single-cell library prepared with our microfluidic workflow. A 5% ratio of PhiX DNA was used in the sequencing runs.

Analysis of Next Generation Sequencing Data—

Sequenced reads were trimmed for adapter sequences (cutadapt), and aligned to the hg19 human genome using bwa-mem after extracting barcode information. After mapping, on target sequences were selected using standard bioinformatics tools (samtools), and barcode sequences were error corrected based on a white list of known sequences. The number of cells present in each tube was determined based on curve fitting a plot of number of reads assigned to each barcode vs. barcodes ranked in decreasing order, similar to what described in Macosko et. al. The total number of cells identified in this manner for a given sample run are presented in FIG. 7 as "Total cells found". A subset of these cells was then identified that had sufficient sequence coverage depth to call genotypes at the 4 non-synonymous variant positions identified in TP53, ASXL1, FLT3 and DNMT3A. This subset of cells is presented as "Number of genotyped cells" in FIG. 7.

GATK 3.7[11] was used to genotype the diagnosis sample with a joint-calling approach. Mutations with a quality score higher than 8,000 were considered accurate variants. The presence of these variants as well as the potential FLT3/ITD were called at a single cell level across the three samples using Freebayes[12]. TP53, ASXL1, FLT3 and DNMT3A genotype cluster analysis was performed using heatmap3 for R[13]. The non-patient Raji cell spike in populations were removed for this analysis.

Bulk Sequencing Using Capture Targeted Sequencing—

We designed a SureSelect™ custom panel of 295 genes (Agilent Technologies, Santa Clara, Calif.) that are recurrently mutated in hematologic malignancies (See FIG. 14). Extracted genomic DNA from bone marrow aspirates was fragmented and bait-captured according to manufacturer protocols. Captured DNA libraries were then sequenced using a HiSeq™ 2000 sequencer (Illumina, San Diego, Calif.) with 76 base-pair paired-end reads.

Hydrogel/Polymer Encapsulation—

In certain embodiments, the disclosure provides methods and apparatus for generating droplets containing a nucleic acid, a barcode oligonucleotide, and a polymeric network. By way of non-limiting example, these methods may be useful for analyzing nucleic acids, identifying a source of a nucleic acid, and determining whether or not different nucleic acids are from one cell or multiple cells.

Some methods comprise flowing individual cells together with a polymeric solution capable of forming microparticles that retain nucleic acids into a carrier fluid such that an emulsion of droplets are formed; breaking the emulsion and collecting the microparticles in an aqueous fluid; and performing combinatorial labeling (Interchangeably, split-pool labeling) on the nucleic acids contained within the microparticles.

Some methods comprise flowing individual cells together with a polymeric material capable of forming a-hydrogel polymer network that retains nucleic acids into a carrier fluid such that an emulsion of droplets are formed; breaking the emulsion and collecting microparticles in an aqueous fluid; performing combinatorial labeling on the nucleic acids contained within the microparticles.

Some methods comprise flowing molecular barcodes and cells together with a polymeric material capable of forming a polymer network or microparticle that retains nucleic acids in a continuous phase carrier fluid such that an emulsion of droplets is formed; breaking the emulsion and collecting polymer networks or microparticles in an aqueous fluid; emulsifying the polymer networks or microparticles containing nucleic acids and molecular barcodes; and labeling the nucleic acids with the barcodes.

Some methods comprise combining molecular barcodes on a polymeric support and cells together into a continuous phase carrier fluid such that an emulsion of droplets are formed; disrupting the polymeric support so that it can capture the nucleic acids; re-polymerizing the support material; breaking the emulsion and collecting microparticles in an aqueous fluid where the nucleic acids are retained within the microparticles; re-emulsifying the microparticles containing nucleic acids and molecular barcodes; and labeling the nucleic acids with the molecular barcodes.

Some methods comprise combining molecular barcodes on a polymer support and cells together into a continuous phase carrier fluid such that an emulsion of droplets are formed; disrupting the polymeric support so that it can capture the cellular nucleic acids; repolymerizing the support material; breaking the emulsion and collecting the microparticles in an aqueous fluid where the cellular nucleic acids are retained within the microparticles; and labeling the nucleic acids with the molecular barcodes.

Certain disclosed embodiments relate to cell analysis using hydrogel (interchangeably, polymer) encapsulation for analyzing nucleic acids within a cell. In such analysis, one or more cell is encapsulated in a porous medium. The porous medium may be, for example, a polymeric material. The nucleic acids of the cell are then retained (or trapped) within the polymer matrix and thereby prevented from diffusing out of the matrix due to the polymer's mesh-like network.

In certain embodiments, the polymer solution may comprise a gel or a hydrogel. In another embodiment, the polymer solution may comprise a functionalized hydrogel configured to capture and retain the cell's nucleic acid.

Polymeric solutions disclosed herein are solutions capable of polymerizing. In some instances, the polymeric solution is capable of polymerizing before droplet formation. In some instances, methods comprise polymerizing the polymeric solution after droplet formation. In some instances, the polymeric solution comprises acrylamide. In some instances, the polymeric solution comprises gelatin. In some instances, the polymeric solution comprises agarose.

In some instances, droplets disclosed herein comprise a gel-like outer layer. The gel-like outer layer may comprise a superabsorbent polymer. The gel-like outer layer may consist or consist essentially of a superabsorbent polymer. In some embodiments, a superabsorbent polymer can be formed by polymerization of acrylic acid blended with sodium hydroxide to form a poly-acrylic acid sodium salt, such as sodium polyacrylate. In some embodiments, a superabsorbent polymer can be made using one or more of a polyacrylamide copolymer, ethylene maleic anhydride copolymer, cross-linked carboxymethylcellulose, polyvinyl alcohol copolymers, cross-linked polyethylene oxide, and starch grafted copolymer of polyacrylonitrile.

In some embodiments, the polymeric solution is capable of forming a hydrogel polymer network that retains nucleic acids. In some instances, microparticles (interchangeably, beads or microspheres) formed by methods disclosed herein comprise the hydrogel polymer network. In some instances, microparticles formed by methods disclosed herein contain the hydrogel polymer network. In some instances, microparticles formed by methods disclosed herein consist essentially of the hydrogel polymer network. In some instances, the nucleic acids are passively prevented from diffusing out of the hydrogel polymer network due to a mesh like character of the hydrogel polymer network.

In certain embodiments, the polymer forms a droplet a microsphere or a bead. One or more cell may be contained within the droplet. The polymer may comprise a material forming a porous polymer matrix. In certain embodiments, the polymer may comprise acrylamide gelatin, agarose or a similar material configured to polymerize after droplet formation.

In one embodiment, a cell or cell material is contained within the polymer matrix. In another embodiment, a cell or cell material is tethered to a polymer substrate.

In some instances, forming an emulsion of polymer and cells may comprise using a polymer- or gel-precursor fluid. A precursor fluid is a liquid formulation configured to form a gel or gel-like substance after exposure to one or more stimuli. The gel-precursor fluid may comprise one or more polymers and/or polymer precursors. In some embodiments, the gel-precursor fluid can comprise a hydrogel. In some embodiments, the gel-precursor fluid comprises acrylamide, polyacrylamide and/or agarose. In some embodiments, the gel-precursor fluid can be an aqueous solution comprising acrylamide and/or agarose. Exposing the one or more polymers and/or polymer precursors to one or more stimuli may facilitate formation of the gel from the precursors. For example, exposure to the stimuli may induce polymerization reactions, including formation of cross-links between polymer chains to thereby facilitate formation of the gel from the gel-precursor fluid. For example, a gel-precursor fluid comprising acrylamide can be exposed to one or more stimuli to form a droplet comprising polyacrylamide. In some embodiments, exposure to one or more stimuli may induce solidification of the gel-precursor fluid. For example, agarose in a gel-precursor fluid may solidify to form an agarose gel when the temperature of the gel-precursor fluid is reduced.

An stimuli, alone or in combination with one or more other stimuli, may be used to convert a precursor fluid (or an inactive polymeric material) into a gel-like or a polymer consistent with the disclosure. In some embodiments, the one or more stimuli may comprise one or more of a physical and chemical stimulus. A physical stimulus may comprise one or more of a temperature, electric field, magnetic field, light or pressure stimulus. A chemical stimulus may comprise exposing the precursor to one or more of a pH, an ionic strength, a solvent composition, and a molecular species stimulus. In some embodiments, a stimulus may be a change in temperature. For example, forming the gel or gel-like substance may comprise altering a temperature of the gel-precursor fluid (e.g., cooling the gel-precursor fluid). In some embodiments, forming the polymer may comprise crystallizing the precursor fluid. Such methods may comprise inducing polymerization and/or formation of cross-links. In some embodiments, the gel-precursor fluid may be exposed to one or more stimuli to induce formation of cross-linkage within and/or between polymers of the gel-precursor fluid. For example, acrylamide in a gel-precursor fluid may be subjected to one or more stimuli such that polymerization occurs to form a droplet comprising polyacrylamide. In some embodiments, forming the gel or gel-like substance may comprise solidifying the gel-precursor fluid. By ways of example, liquid agarose of a droplet may be cooled such that the liquid agarose can solidify to form a cell trapped inside an agarose network.

In certain embodiment, a polymerizing agent may be added to aid in polymerization of the droplet. In other embodiment, the polymer droplet may be formed by heating or thermocycling the polymeric material. In still other embodiment, a catalyst or an in initiator may be used to start polymerization of the droplet.

In certain embodiments, lysis reagent may be added at or prior to encapsulation by a polymer to help release the DNA from its respective cell. In another embodiment, a cell is polymerized with a porous polymer to form a microsphere or a bead. After polymerization, a lysis reagent is perfused into the bead to release the DNA from the cell while entrapping the cell within the polymer matrix of the bead.

In some embodiments, droplets disclosed herein comprise nucleic acids, wherein the nucleic acids are from a cell. In some instances, a droplet comprises a whole, intact cell. In some instances, a droplet comprises a cell lysate. In some instances, a droplet comprises a partially lysed cell. In some instances, methods disclosed herein comprise lysing a cell before containing the nucleic acids thereof in a droplet. In some instances, methods disclosed herein comprise lysing a cell after containing the nucleic acids thereof in a droplet. In some instances, methods comprise containing a cell and cell lysis reagents in a droplet. In some instances, methods comprise contacting a droplet with a cell lysis reagent. In some instances, methods comprise injecting a droplet with a cell lysis reagent. In some instances, methods comprise flowing droplets into a cell lysis reagent. In some instances, methods comprise flowing cell lysis reagent into a carrier fluid comprising droplets. In some instances, the lysis reagent comprises a detergent. In some instances, the lysis reagent comprises a protease. In some instances, the lysis reagent comprises a lysozyme. In some instances, the lysis reagent comprises a protease. In some instances, the lysis reagent comprises an alkaline buffer.

In certain embodiments, the disclosed methods comprise contacting the hydrogel beads with a barcode oligonucleotide, wherein the barcode oligonucleotide is delivered on a solid support. Solid supports or solid particles, such as solid supports comprising one or more surfaces coated with oligonucleotides configured for use in single-cell barcoding, are often difficult to manipulate microfluidically. In some embodiments, the solid support comprises a polymeric material. By way of non-limiting example, the polymeric material may be poly(methyl methacrylate), polycarbonate, or polystyrene. In some embodiments, the solid support can comprise silica. In some embodiments, the solid support can comprise a metal, including one or more of aluminum and steel. The elastic modulus of the solid support can depend on its compositions. The rigid solid supports may have a high elastic modulus. For example, the solid supports as envisioned herein can have an elastic modulus, such as a Young's modulus, between about 0.5 GPa to about 200 GPa. Encapsulating solid supports with an outer gel layer can advantageously simplify the microfluidic handling of the solid supports. Encapsulating the solid supports can advantageously provide soft-gel beads which are deformable, and/or soft-gel beads which can be selected using optical detection and/or magnetic attraction techniques.

Figure 15:
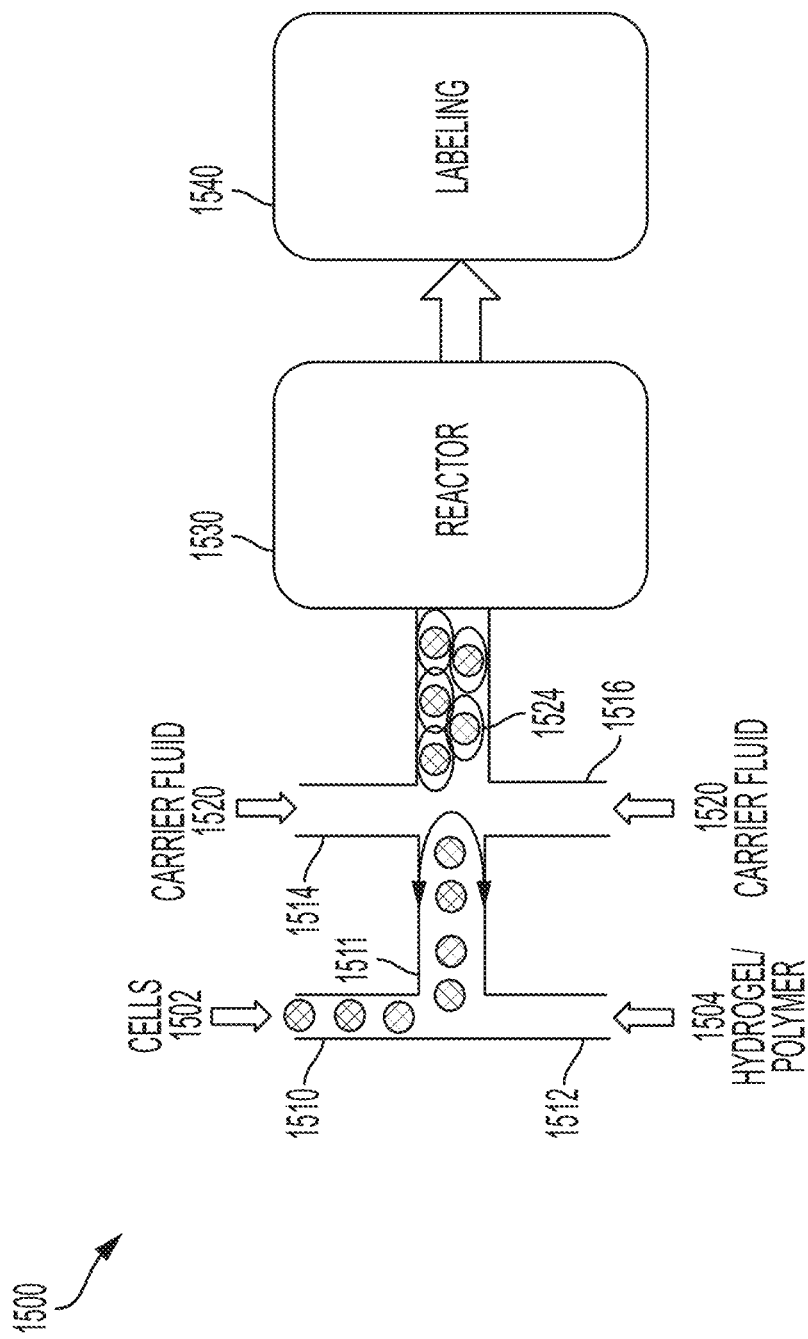
FIG. 15 schematically illustrates a platform or device for implementing hydrogel and/or polymer cell encapsulation according to one embodiment of the disclosure.

FIG. 15 schematically illustrates a portion of a platform, device or apparatus for implementing hydrogel and/or polymer cell encapsulation according to one embodiment of the disclosure. In FIG. 15, cells 1502 are provided at inlet 1510 of device platform 1500. Hydrogel polymer material 1504 is supplied to inlet 1512 of device 1500. The cell stream and polymer steam merge and cause cells 1502 to flow within the stream 1511. A carrier fluid 1520 (as described above) is directed to inlets 1514 and 1516 of device 1500. Admixture of streams 1511 and carrier fluid 1520 creates an emulsion.

In some embodiments, the emulsifying step of FIG. 15 is performed under microfluidic control. Emulsifying may comprise transporting a plurality of controllably spaced droplets in a first fluid through a first microfluidic channel and flowing a carrier fluid in a second microfluidic channel such that the first fluid and the immiscible carrier fluid intersect as shown in FIG. 15. The carrier fluid may define an immiscible fluid. The first microfluidic channel and the second microfluidic channel can join at a junction such that the first fluid and the immiscible carrier fluid can intersect to reliably generate an emulsion of cells with a polymer solution.

In an exemplary embodiment, a polymerizing reagent (not shown) may be included in stream 1520 along with the carrier fluid. The addition of the polymerizing agent is optional and may be implemented based on the hydrogel/polymer 1504 configuration.

In still another embodiment, a lysing reagent may be optionally added to one or more of the incoming streams. For example, the lysing reagent may be included in the hydrogel/polymer stream 1504.

In yet another embodiment, one or more optional reagents may be included in the inlets 1510, 1512, 1514 and 1516. Alternatively, additional inlets may be made through device 1500 to include additional material. For example, reagents such as polymerase may be optionally added depending on the droplet configuration. Other material that may have non-deleterious effects on the cell may also be included.

In certain embodiments a reactor may be optionally used to help polymerize the hydrogel. In FIG. 15, the emulsion stream 1524 is then directed to reactor 1530. Reactor 1530 can polymerize the polymer (e.g., hydrogel) and breaks the emulsion to release droplets (e.g., beads or microspheres). In certain embodiments where a thermosetting polymer is used, reactor 1530 may comprise a thermal reactor to allow hydrogel bead formation.

If, on the other hand, a polymerizing agent is used (e.g., added along carrier fluid 1520), reactor 1530 may comprise a containment to allow the polymerization reaction to take place.

In one embodiment of the disclosure, emulsion stream 1524 comprise one or more cells within a polymer microsphere or bead. The proceeding stream is directed to polymerizer 1530 to polymerize the polymer (or hydrogel) around the cell.

After the hydrogel is polymerized and the emulsions are broken to form hydrogel beads, the beads are labeled as schematically illustrated in FIG. 15 as labeling 1540. Conventional labeling methods or labeling techniques described above may be used equally without departing from the disclosed principles.

In certain embodiment, the polymerases or nucleic acid synthesis reagents could be added during split-pool labeling at one or multiple points following breaking of the initial emulsion and isolating the polymeric hydrogel beads with cell nucleic acids.

In some embodiments, split-pool (interchangeably, combinatorial labeling) labeling of nucleic acids may be used. The nucleic acids subjected to split pool labeling can be retained within polymer matrix of the microparticles disclosed herein (e.g., microparticles comprising a hydrogel polymer network.) Methods of split pool labeling, may comprise splitting a pool of droplets, wherein a droplet of the pool contains an individual cell or lysate thereof, into at least a first container to contain a first portion of droplets and a second container to contain a second portion of droplets, contacting the first portion of droplets with a first barcode oligonucleotide to produce first barcoded droplets, and contacting the second portion of droplets with a second barcode oligonucleotide to produce second barcoded droplets. The first barcode oligonucleotide can be different from the second barcode oligonucleotide. Methods may comprise pooling the first barcoded droplets and second barcoded droplets, subsequently moving a first barcoded droplet into a third container and contacting the first barcoded droplet with a third barcode oligonucleotide to produce a droplet containing a first barcode oligonucleotide and a third barcode oligonucleotide, thereby distinguishing it from droplets that do not have this combination of barcode oligonucleotides. In general, the third barcode oligonucleotide can be different from the first and second barcode oligonucleotides.

Multiple nucleic acids in the droplet may be contacted with barcode oligonucleotides such that multiple rounds of split pool labeling result in labeling multiple nucleic acids in the droplet with a combination of barcode oligonucleotides, the combination being unique to the droplet, and thus, unique to the cell. For instance, each round may comprise contacting the nucleic acids with a new set of barcode oligonucleotides relative to barcode oligonucleotides previously received. Often, barcode oligonucleotides from any given round are different from those of previous rounds.

However, in some instances, barcode oligonucleotides can be used repeatedly. In general, barcode oligonucleotides used in the same round are different. Each time the droplets are pooled and split again, there is a likelihood that at least some droplets that have an identical combination of barcode oligonucleotides will be split into containers receiving new barcode oligonucleotides unique from one another, thereby producing two groups of droplets with a unique combination of barcode oligonucleotides relative to one another.

Split pool labeling may comprise labeling nucleic acids in the droplets with barcode oligonucleotides. For instance, a first barcoded droplet generally comprises a first barcoded nucleic acid. Often, a first barcoded droplet comprises a plurality of first barcoded nucleic acids due to the fact that there are multiple nucleic acids in each droplet. In some instances, labeling comprises hybridizing a nucleic acid with a barcode oligonucleotide. In some instances, labeling comprises ligating a nucleic acid with a barcode oligonucleotide.

In some instances, methods may include contacting a droplet with barcode oligonucleotides at least twice. In some instances, methods comprise contacting a droplet with barcode oligonucleotides at least three times. In some instances, methods comprise contacting a droplet with barcode oligonucleotides at least five times. In some instances, methods comprise contacting a droplet with barcode oligonucleotides at least eight times. In some instances, methods comprise contacting a droplet with barcode oligonucleotides at least ten times. In some instances, methods comprise contacting a droplet with barcode oligonucleotides at least twelve times. In some instances, methods comprise contacting a droplet with barcode oligonucleotides not more than eight times. In some instances, methods comprise contacting a droplet with barcode oligonucleotides not more than ten times. In some instances, methods comprise contacting a droplet with barcode oligonucleotides not more than twelve times.

In an exemplary embodiment, a so-called split-pool labeling technique may be used to label the cells contained in the hydrogel beads. To implement split-pool labeling according to one embodiment of the disclosure, the beads are first dispersed onto a well plate. The well plate may comprise an array of wells formed within or on a substrate. Each well may be configured to receive one bead. Next, the nucleic acid within each bead is labeled with a first barcode. Once, the first labeling step is complete, the beads are pooled together at a container. The pooling of the beads allow the beads to distribute and disperse within the pool. Next, the hydrogel beads are once again dispersed into the well array such that each well may substantially contain one hydrogel bead. Next, the nucleic acid of each hydrogel bead is labeled again with a second bar code. The first and the second barcoding make it highly probable that each cell obtains a unique combination of barcodes, thereby allowing its identification from other cells more likely.

Figure 16:
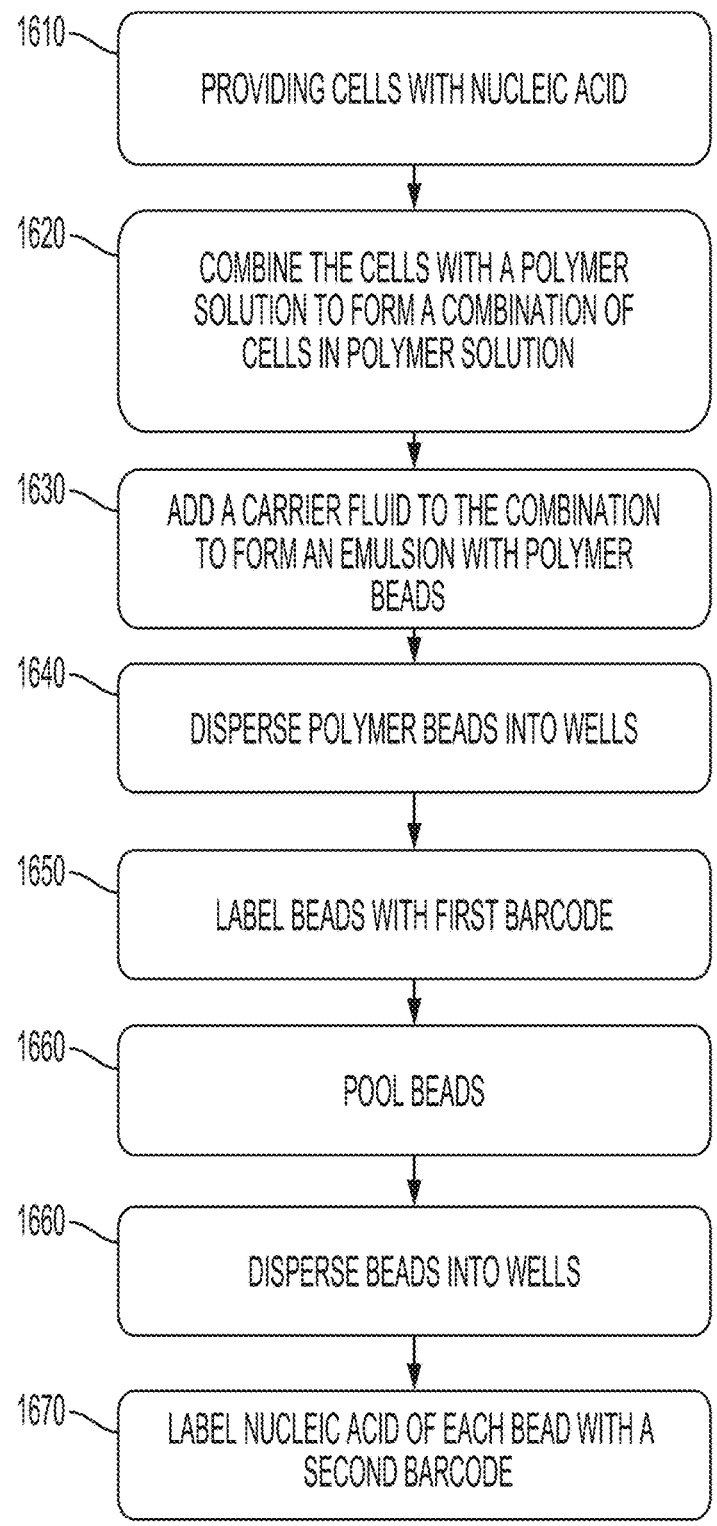
FIG. 16 illustrates a flow diagram for implementing a process according to one embodiment of the disclosure.

FIG. 16 illustrates a flow diagram for implementing a process according to one embodiment of the disclosure. The process of FIG. 16 starts at step 1610 by providing a plurality of cells with each cell having a respective nucleic acid. At step 1620, the cells are combined with a polymer solution to form a combination of cells in a polymer solution. In one embodiment, the polymer solution may comprise a gel or a hydrogel. In another embodiment, the polymer solution may comprise a functionalized hydrogel configured to capture and retain the cell's nucleic acid.

At step 1630, a carried fluid is added to the combination to form an emulsion. In certain embodiments, the emulsion may comprise cells having nucleic acid and the polymer solution. In one embodiment, the carrier fluid addition causes formation of droplets. The droplets may be shaped as a bead or microspheres. An exemplary droplet may comprise a cell encapsulated in a hydrogel shell.

Additional steps may be taken to start or to complete polymerization of the polymer shells. In an exemplary embodiment, a polymerizer and/or other additives may be added to the carrier fluid. In still another exemplary embodiment, a lysing reagent may be added to the carrier fluid or to the hydrogel polymer solution. In an exemplary implementation, the polymer agent may be allowed to polymerized using thermal polymer setting. Once polymerization is substantially complete, polymer beads having cells are formed.

In an optional step, a cell contained within a polymer bead may be allowed to release its nucleic acid. The release of nucleic acid may be aided by presence of a lysing reagent. In one embodiment, the polymeric surface of the bead may define a porous surface to allow a lysing agent to perfuse therethrough. The lysing agent may then release the nucleic acid from the cell. In one embodiment, the release nucleic acid is trapped inside the polymer matrix of the bead.

In an exemplary embodiment, the polymerases or nucleic acid synthesis reagents could be added during split-pool labeling at one or multiple points following breaking of the initial emulsion and isolating the polymeric hydrogel beads with cell nucleic acids.

While not specifically stated in FIG. 16, step 1630 may include the following additional steps: (1) allowing the polymer solution to polymerize in droplets, and (2) breaking the emulsion and isolating an aqueous solution with polymerized hydrogels containing cell nucleic acid.

At step 1640, beads are added to an array of wells such that substantially each bead is at a well. Step 1640 may optionally include other steps, for example, sieving the beads out of the solution.

At step 1650, the nucleic acid contained in the bead is labeled with a first barcode. The barcode labeling of the nucleic acid may be implemented according to conventional methods. In an exemplary implementation, the polymerized beads housed in respective wells are labeled by contacting the polymer-trapped nucleic acids with a plurality of barcodes. The beads may then be assayed as need to identify their sequence. The process FIG. 16 may optionally end at step 1650.

Optionally, a second barcode label may be added to the nucleic acid of the polymer beads to further distinguish each bead/nucleic acid. The second labeling process is shown at steps 1660 to 1670. Specifically, at step 1660, the barcoded beads are dispersed into wells for a second time. A second barcode is introduced to the beads such that substantially each nucleic acid additionally couples to a second barcode. The second barcode further distinguishes each bead/nucleic acid.

The following examples are presented to further illustrates different embodiments of the disclosure. These examples are non-limiting and illustrative.

Example 1 is directed to a method to detect one or more mutations in tumor cells, the method comprising: encapsulating at least one cell and a lysis reagent in a carrier fluid to form a droplet, wherein the cell originates from a tumor and the cell comprises a genomic DNA; lysing the cell to release the genomic DNA and thereby form a droplet containing the genomic DNA; introducing a one or more cell identifiers and one or more primers specific to a plurality of regions of the genomic DNA; and thermocycling the droplet to amplify the plurality of regions of genomic DNA and to incorporate the one or more cell identifiers thereby producing amplified DNA with the cell identifiers; wherein once the cell identifier is incorporated into the amplified DNA, the amplified regions are sequenced and at least one DNA mutation is identified for the tumor cells.

Example 2 is directed to the method of example 1, wherein a plurality of DNA mutations are identified for the tumor cells.

Example 3 is directed to the method of example 1, wherein the plurality of DNA mutations are identified substantially simultaneously for the tumor cells.

Example 4 is directed to the method of example 1, wherein the cell identifier is an oligonucleotide that serves as a cell barcode.

Example 5 is directed to the method of example 1, wherein the specific primers target 5-500 loci on the genomic DNA. In one embodiment, the specific primers target 10 or more loci on the genomic DNA.

Example 5 is directed to the method of example 1, wherein the specific primers target 10-500 loci on the genomic DNA. In one embodiment, the specific primers target 10-2,000 loci on the genomic DNA.

Example 6 is directed to the method of example 1, wherein the specific primers target 500-20,000 loci on the genomic DNA. In one embodiment, the specific primers target 500-2,000 loci on the genomic DNA.

Example 7 is directed to the method of example 1, wherein the lysis reagent comprises a protease.

Example 8 is directed to the method of example 1, wherein the specific primers target 2,000-100,000 loci on the genomic DNA.

Example 9 is directed to the method of example 1, wherein the number of tumor cells analyzed are about 10-1,000. In one embodiment, the number of tumor cells analyzed are about 100-1,000,000. In another embodiment, the detected mutation defines at least one attribute that correlates to a known disease.

Example 10 is directed to the method of example 1, wherein the number of tumor cells analyzed are about 1,000-100,000. In another embodiment, the number of tumor cells analyzed are about 10-100,000.

Example 11 is directed to the method of example 1, wherein the number of tumor cells analyzed are about 100,000-1,000,000.

Example 12 is directed to the method of example 1, wherein the detected mutation defines at least one attribute that correlates to a known disease.

Example 13 is directed to the method of example 1, wherein presence of the mutated cell is prognostic of a disease relapse.

Example 14 is directed to the method of example 1, wherein the at least one cell originates from a patient in disease remission.

Example 15 is directed to a method to detect one or more mutations in cells, the method comprising: forming a first droplet in a carrier fluid, the droplet having a tumor cell; lysing the tumor cell and releasing the genomic DNA to provide a released genomic DNA; forming a second droplet, the second droplet having the released genomic DNA, one or more cell identifier and one or more primers specific to a plurality of regions of the genomic DNA; and thermocycling the second droplet to amplify the plurality of regions of genomic DNA and to incorporate the one or more cell identifiers thereby producing amplified DNA with cell identifiers; wherein once the one or more cell identifiers are incorporated into the amplified DNA and wherein the amplified regions are sequenced and at least one DNA mutation is identified for the tumor cells.

Example 16 is directed to the method of example 15, wherein a plurality of DNA mutations are identified for the tumor cells.

Example 17 is directed to the method of example 15, wherein the plurality of DNA mutations are identified substantially simultaneously for the tumor cells.

Example 18 is directed to the method of example 15, wherein the specific primers target 10 or more loci on the genomic DNA.

Example 19 is directed to the method of example 15, wherein the specific primers target 10-500 loci on the genomic DNA. In one embodiment, the specific primers target 5 or more loci on the genomic DNA.

Example 20 is directed to the method of example 15, wherein the specific primers target 500-2,000 loci on the genomic DNA.

Example 21 is directed to the method of example 15, wherein the specific primers target 2,000-100,000 loci on the genomic DNA.

Example 22 is directed to the method of example 15, wherein the lysis reagent comprises a protease.

Example 23 is directed to the method of example 15, wherein the number of tumor cells analyzed are about 10-1,000.

Example 24 is directed to the method of example 15, wherein the number of tumor cells analyzed are about 1,000-100,000

Example 25 is directed to the method of example 15, wherein the number of tumor cells analyzed are about 100,000-1,000,000

Example 26 is directed to the method of example 15, wherein the detected mutation defines at least one attribute that correlates to a known disease.

Example 27 is directed to the method of example 15, wherein presence of the mutated cell is prognostic of a disease relapse.

Example 28 is directed to the method of example 15, wherein the at least one cell originates from a patient in disease remission.

Example 29 is directed to a system to detect one or more mutations in tumor cells, comprising: a first microfluidic channel to encapsulate at least one cell and a lysis reagent in a carrier fluid to form a droplet, wherein the cell originates from a tumor; an incubator to lyse the cell to release the genomic DNA and thereby form a droplet containing the genomic DNA; a second microfluidic channel to introduce a cell identifier and one or more primers specific to a plurality of regions of the genomic DNA to the droplet; and a thermocycler to thermocycle the droplet to amplify the genomic DNA and to incorporate cell identifiers into the genomic DNA to thereby produce a plurality of amplified DNA with identified loci; wherein once the cell identifier is incorporated into the amplified DNA, the identified loci are sequenced and at least one DNA mutation is identified for the tumor cells.

Example 30 is directed to the system of example 29, wherein a plurality of DNA mutations are identified for the tumor cells.

Example 31 is directed to the system of example 29, wherein the plurality of DNA mutations are identified substantially simultaneously for the tumor cells.

Example 32 is directed to the system of example 29, wherein the specific primers target 10 or more loci on the genomic DNA.

Example 33 is directed to the system of example 29, wherein the specific primers target 10-500 loci on the genomic DNA.

Example 34 is directed to the system of example 29, wherein the specific primers target 500-2,000 loci on the genomic DNA.

Example 35 is directed to the system of example 29, wherein the specific primers target 2,000-100,000 loci on the genomic DNA.

Example 36 is directed to the system of example 29, wherein the lysis reagent comprises a protease.

Example 37 is directed to the system of example 29, wherein the number of tumor cells analyzed are about 10-1,000.

Example 38 is directed to the system of example 29, wherein the number of tumor cells analyzed are about 1,000-100,000

Example 39 is directed to the system of example 29, wherein the number of tumor cells analyzed are about 100,000-1,000,000.

Example 40 is directed to the system of example 29, wherein the detected mutation defines at least one attribute that correlates to a known disease.

Example 41 is directed to the system of example 29, wherein presence of the mutated cell is prognostic of a disease relapse.

Example 42 is directed to the system of example 29, wherein the at least one cell originates from a patient in disease remission.

Example 43 is directed to a system to detect one or more mutations in cells, comprising: a first microfluidic channel to form a first droplet in a carrier fluid, the droplet having a tumor cell; an incubator to lyse the tumor cell and to release the genomic DNA; a second microfluidic channel to form a second droplet, the second droplet having a cell identifier and one or more primers specific to a plurality of regions of the genomic DNA; and a thermocycler to thermocycle the second droplet to amplify the genomic DNA and to incorporate the identifier into the genomic DNA to thereby produce a plurality of amplified DNA with identified loci; wherein once the cell identifier is incorporated into the amplified DNA, the identified loci are sequenced and at least one DNA mutation is identified for the tumor cells.

Example 44 is directed to the system of example 43, wherein a plurality of DNA mutations are identified for the tumor cells.

Example 45 is directed to the system of example 43, wherein the plurality of DNA mutations are identified substantially simultaneously for the tumor cells.

Example 46 is directed to the system of example 43, wherein the specific primers target 10 or more loci on the genomic DNA.

Example 47 is directed to the system of example 43, wherein the specific primers target 10-500 loci on the genomic DNA.

Example 48 is directed to the system of example 43, wherein the specific primers target 500-2,000 loci on the genomic DNA.

Example 49 is directed to the system of example 43, wherein the specific primers target 2,000-100,000 loci on the genomic DNA.

Example 50 is directed to the system of example 43, wherein the lysis reagent comprises a protease.

Example 51 is directed to the system of example 43, wherein the number of tumor cells analyzed are about 10-1,000.

Example 52 is directed to the system of example 43, wherein the number of tumor cells analyzed are about 1,000-100,000

Example 53 is directed to the system of example 43, wherein the number of tumor cells analyzed are about 100,000-1,000,000

Example 54 is directed to the system of example 43, wherein the detected mutation defines at least one attribute that correlates to a known disease.

Example 55 is directed to the system of example 43, wherein presence of the mutated cell is prognostic of a disease relapse.

Example 56 is directed to the system of example 43, wherein the at least one cell originates from a patient in disease remission.

Example 57 is directed to a method for analyzing nucleic acids within a cell comprising: (a) flowing individual cells together with a polymeric solution capable of forming microparticles that retain nucleic acids into a carrier fluid such that an emulsion of droplets are formed; (b) breaking the emulsion and collecting the microparticles in an aqueous fluid; and (c) performing combinatorial labeling on the nucleic acids contained within the microparticles.

Example 58 is directed to the method of example 57, wherein the polymeric solution comprises a polymer selected from acrylamide, gelatin, and agarose.

Example 59 is directed to the method of example 57, wherein the polymeric solution is capable of polymerizing after droplet formation.

Example 60 is directed to the method of example 57, comprising incorporating an oligonucleotide into the polymeric solution. The oligonucleotide can be one of an acidite oligonucleotide containing a poly-dT sequence to hybridize to a poly-A tail of cellular mRNA and keep them retained within the hydrogel/microsphere.

Example 61 is directed to the method of example 60, comprising capturing or hybridizing the nucleic acids with the oligonucleotide.

Example 62 is directed to the method of example 60, wherein the oligonucleotide comprises a sequence complementary to at least one of the nucleic acids.

Example 63 is directed to the method of example 62, wherein the oligonucleotide contains a poly-dT sequence, and at least one of the nucleic acids comprises a poly-A tail the oligonucleotide thereby retaining at least one of the nucleic acids within the microsphere hydrogels.

Example 64 is directed to a method for analyzing nucleic acids within a cell comprising: (a) flowing individual cells together with a polymeric material capable of forming a hydrogel polymer network that retains nucleic acids into a carrier fluid such that an emulsion of droplets are formed; (b) breaking the emulsion and collecting microparticles in an aqueous fluid; and (c) performing combinatorial labeling on the nucleic acids contained within the microparticles.

Example 65 is directed to the method of example 64, wherein the nucleic acids are retained within the hydrogel polymer network.

Example 66 is directed to the method of example 64, wherein the nucleic acids are passively prevented from diffusing out of the hydrogel polymer network due to a mesh like character of the hydrogel polymer network.

Example 66 is directed to the method of any preceding example, comprising split pool labeling of the nucleic acids.

Example 67 is directed to the method of any preceding example, comprising combinatorial split pool labeling of the nucleic acids.

Example 68 is directed to the method of example 67, wherein combinatorial split pool labeling is performed with an oligonucleotide ligated onto the nucleic acids.

Example 69 is directed to the method of example 67, wherein combinatorial split pool labeling comprises nucleic acid synthesis.

Example 70 is directed to the method of example 64, comprising incorporating barcodes into the microparticles.

Example 71 is directed to a method for analyzing nucleic acids within a cell comprising: (a) flowing molecular barcodes and cells together with a polymeric material capable of forming a polymer network that retains nucleic acids in a continuous phase carrier fluid such that an emulsion of droplets is formed; (b) breaking the emulsion and collecting polymer networks in an aqueous fluid; (c) emulsifying the polymer networks containing nucleic acids and molecular barcodes; and (d) labeling the nucleic acids with the barcodes.

Example 72 is directed to a method for analyzing nucleic acids within a cell comprising: (a) flowing molecular barcodes and cells together with a polymeric material capable of forming microparticles that retains nucleic acids in a continuous phase carrier fluid such that an emulsion of droplets is formed; (b) breaking the emulsion and collecting the microparticles in an aqueous fluid; (c) emulsifying the or microparticles containing nucleic acids and molecular barcodes; and (d) labeling the nucleic acids with the barcodes.

Example 73 is directed to a method of example 71 or 72, wherein emulsifying is performed under microfluidic control.

Example 74 is directed to the method of example 71 or 72, wherein emulsifying comprises agitation or shaking.

Example 75 is directed to a method for analyzing nucleic acids within a cell comprising: (a) combining molecular barcodes on a polymeric support and cells together into a continuous phase carrier fluid such that an emulsion of droplets are formed; (b) disrupting the polymeric support so that it can capture the nucleic acids; (c) re-polymerizing the support material to form microparticles from the droplets; (d) breaking the emulsion and collecting microparticles in an aqueous fluid where the nucleic acids are retained within the microparticles; (e) re-emulsifying the microparticles containing nucleic acids and molecular barcodes; and (f) labeling the nucleic acids with the molecular barcodes.

Example 76 is directed to the method of example 74 or 75, wherein combining is performed under microfluidic control.

Example 77 is directed to the method of example 74 or 75, wherein combining comprises at least one of agitation and shaking.

Example 78 relates to a method for analyzing nucleic acids within a cell comprising: (a) Combining molecular barcodes on a polymer support and cells together into a continuous phase carrier fluid such that droplets are formed; (b) disrupting the polymeric solid support so that it can capture the cellular nucleic acids and then repolymerizing the support material; (c) breaking the emulsion and collecting the microsphere hydrogels in an aqueous fluid where the cellular nucleic acids are retained within the microsphere; and (d) using the barcode to label the nucleic acids from the cells with a reaction.

Example 79 relates to the method of example 78, wherein step (a) is performed under microfluidic control.

Example 80 relates to the method of example 78, wherein step (a) is done with agitation or shaking.

Example 81 relates to a method for analyzing nucleic acids within a cell, comprising: (a) Combining molecular barcodes on a polymer support and cells together into a continuous phase carrier fluid to form a microsphere such that droplets are formed; (b) disrupting the polymeric solid support so that it can capture the cellular nucleic acids and then re-polymerizing the support material; (c) breaking the emulsion and collecting the microsphere hydrogels in an aqueous fluid where the cellular nucleic acids are retained within the microsphere; (d) re-emulsifying the microspheres containing nucleic acids and molecular barcodes; and (e) using the barcode to label the nucleic acids with a reaction.

Example 82 relates to the method of example 81, wherein step (a) is performed under microfluidic control.

Example 83 relates to the method of example 81, wherein step (a) is performed with agitation or shaking.

Example 84 relates to the method of example 81, wherein step (c) is performed under microfluidic control.

Example 85 relates to the method of example 81, wherein step (c) is performed with agitation or shaking.

Example 86 relates to an apparatus for analyzing nucleic acids within a cell comprising: means for flowing a plurality of individual cells together with a material capable of forming a polymer or microsphere into a carrier fluid to form a plurality of microspheres in an emulsions, wherein each cell further contains a respective nucleic acid and wherein each of the plurality of microspheres is configured to retain a respective nucleic acid; means for breaking the emulsion and collecting the one or more microspheres in an aqueous fluid; and means for performing combinatorial labeling on the nucleic acids contained within the microspheres hydrogels.

Example 87 relates to an apparatus for analyzing nucleic acids within a cell, comprising: (a) means for combining a plurality of molecular barcodes on a polymeric support with a plurality of cells in a carrier fluid to form a plurality of microsphere in an emulsion, wherein the carrier fluid defines a continuous phase fluid; (b) means for disrupting the polymeric support to capture a plurality of nucleic acids contained within a respective plurality of cells and then re-polymerizing the support material; (c) means for breaking the emulsion and collecting the microspheres in an aqueous fluid wherein each of the plurality of nucleic acids is retained within a respective one of the plurality of microspheres, each collected microsphere having a respective nucleic acid and an associated barcode; (d) means for re-emulsifying the collected microspheres; and (e) means for using the associated barcode to label the associated nucleic acid with a reaction.

Embodiments described above illustrate but do not limit this application. While a number of exemplary aspects and embodiments have been discussed above, those of skill in the art will recognize certain modifications, permutations, additions and sub-combinations thereof. Accordingly, the scope of this disclosure is defined only by the following claims.

What is claimed is:

1. A method for analyzing nucleic acids within a cell, comprising:
   (a) combining a plurality of molecular barcodes on a polymeric support with a plurality of cells in a carrier fluid to form a plurality of microsphere in an emulsion, wherein the carrier fluid defines a continuous phase fluid;
   (b) disrupting the polymeric support to capture a plurality of nucleic acids contained within a respective plurality of cells and then re-polymerizing the support material;
   (c) breaking the emulsion and collecting the microspheres in an aqueous fluid wherein each of the plurality of nucleic acids is retained within a respective one of the plurality of microspheres, each collected microsphere having a respective nucleic acid and an associated barcode;

(d) re-emulsifying the collected microspheres; and (e) using the associated barcode to label the associated nucleic acid with a reaction.

2. The method of claim 1, wherein step (a) is performed under microfluidic control.

3. The method of claim 1, wherein step (a) is done with agitation or shaking.

4. The method of claim 1, wherein step (c) is performed under microfluidic control.

5. The method of claim 1, wherein step (c) is done with agitation or shaking.

6. The method of claim 1, wherein the polymeric support defines a polymeric solid support.

* * * * *